US008624203B2

(12) United States Patent
Tullo et al.

(10) Patent No.: US 8,624,203 B2
(45) Date of Patent: Jan. 7, 2014

(54) CONVEYOR STERILIZATION

(75) Inventors: Joe Tullo, Toronto (CA); Grant Jeffery Caven, Toronto (CA); Paul Jeffery Payne, Toronto (CA); Stylianos Derventzis, Ajax (CA)

(73) Assignee: JLT & Associates, Inc., Toronto (CA)

( * ) Notice: Subject to any disclaimer, the term of this patent is extended or adjusted under 35 U.S.C. 154(b) by 163 days.

(21) Appl. No.: 13/397,963

(22) Filed: Feb. 16, 2012

(65) Prior Publication Data
US 2012/0211645 A1 Aug. 23, 2012

Related U.S. Application Data

(60) Provisional application No. 61/445,774, filed on Feb. 23, 2011.

(51) Int. Cl.
*A61L 2/10* (2006.01)
(52) U.S. Cl.
USPC ......... 250/492.1; 198/493; 198/494; 198/495
(58) Field of Classification Search
USPC ............. 250/492.1, 454.11, 455.11; 198/493, 198/494, 495, 496
See application file for complete search history.

(56) References Cited

U.S. PATENT DOCUMENTS

| 2,017,079 | A | * | 10/1935 | Steerup | 422/186.21 |
|---|---|---|---|---|---|
| 4,776,267 | A | | 10/1988 | Harris | |
| 5,114,670 | A | | 5/1992 | Duffey | |
| 5,925,885 | A | | 7/1999 | Clark et al. | |
| 6,028,315 | A | | 2/2000 | Bailey et al. | |
| 6,429,444 | B1 | | 8/2002 | Korenev et al. | |
| 6,551,407 | B2 | | 4/2003 | Drzal et al. | |
| 6,576,188 | B1 | | 6/2003 | Rose et al. | |
| 6,649,921 | B1 | | 11/2003 | Cekic | |
| 6,710,357 | B1 | | 3/2004 | Schweitzer | |
| 6,851,454 | B2 | | 2/2005 | Koerner | |
| 6,851,545 | B1 | | 2/2005 | Carter | |
| 7,234,586 | B1 | | 6/2007 | Newman | |
| 7,304,259 | B2 | | 12/2007 | Schwarz et al. | |
| 7,638,780 | B2 | * | 12/2009 | Kilburn et al. | 250/492.1 |
| 2006/0219524 | A1 | | 10/2006 | Kelly | |
| 2008/0199353 | A1 | | 8/2008 | Mlodzinski | |
| 2010/0178201 | A1 | | 7/2010 | Tribelsky et al. | |
| 2010/0243410 | A1 | | 9/2010 | Hall et al. | |
| 2011/0308917 | A1 | | 12/2011 | Lathem | |

FOREIGN PATENT DOCUMENTS

WO   WO 01/11993 A1   2/2001

OTHER PUBLICATIONS

"The International Search Report and the Written Opinion of the International Searching Authority, or the Declaration for International Application No. PCT/CA2012/050111," filed Jun. 5, 2012.

* cited by examiner

*Primary Examiner* — Tony Ko
(74) *Attorney, Agent, or Firm* — Brett A. Schenck; Walker & Jocke

(57) ABSTRACT

A sterilizing system for sterilizing a continuous loop conveyor belt of a conveyor system is provided. The conveyor system includes a drive operatively connected to the conveyor belt and operative to move the belt between upper and lower flight paths. The upper flight path includes an exposed surface for receiving items. The sterilizing system includes a housing that is configured to at least partially cover the lower flight path. An ultraviolet light source is positioned in the interior of the housing. The light source is operative to emit ultraviolet light on the belt at the lower flight path to sanitize the belt.

9 Claims, 16 Drawing Sheets

CONVEYOR STERILIZATION

CROSS-REFERENCE TO RELATED APPLICATIONS

This application claims benefit under 35 U.S.C. §119(e) of Provisional Application No. 61/445,774 filed Feb. 23, 2011, the disclosure of which is incorporated herein by reference in its entirety.

TECHNICAL FIELD

This invention relates to a sterilizing system for sterilizing a continuous loop conveyor belt of a conveyor system that may be classified in U.S. Class 198, Subclass 494.

BACKGROUND ART

A conveyor-belt checkout stand may be used to transport groceries or other items toward the cashier and away from the cashier to the bagging area. In a conveyor-belt type checkout stand, a synthetic conveyor belt, typically of rubber or plastic, is supported on each end by a roller. These rollers provide a tension between themselves to retain the conveyor belt in position. The belt is also equipped with a drive motor that advances the belt around the rollers. In use, a customer approaches a checkout stand and places his groceries or other items on the conveyor belt. Either by manual control or by an automated device, the rollers begin to rotate, thereby advancing the surface of the conveyor belt containing the groceries or other items toward the cashier. Sterilizing systems for sterilizing the conveyor belt may be provided to maintain a sanitary environment.

Sterilizing systems for sterilizing the conveyor belt of a conveyor system may benefit from improvements.

OBJECTS OF EXEMPLARY EMBODIMENTS

It is an object of exemplary embodiments to provide an improved sterilizing system for sterilizing the conveyor belt of a conveyor system.

It is another object of exemplary embodiments to provide a sterilizing system for sterilizing the conveyor belt of a conveyor system having improved operating and servicing capabilities.

It is a further object of exemplary embodiments to provide a sterilizing system for sterilizing the conveyor belt of a conveyor system that can be easily installed on existing conveyor system.

It is a further object of exemplary embodiments to provide a sterilizing system for sterilizing the conveyor belt of a conveyor system that can accommodate belts of different widths.

It is a further object of exemplary embodiments to provide a sterilizing system for sterilizing the conveyor belt of a conveyor system in which the components of the sterilizing system and conveyor system can be monitored.

It is a further object of the exemplary embodiment to control the amount (or intensity) of ultraviolet radiation incident on the exposed surface of the conveyor belt.

Further objects of exemplary embodiments will be made apparent in the following Detailed Description of Exemplary Embodiments and the appended claims.

The foregoing objects are accomplished in one exemplary embodiment by a sterilizing system for sterilizing a continuous loop conveyor belt of a conveyor system, wherein the conveyor system includes a drive operatively connected to the conveyor belt, wherein the drive is operative to move the belt between upper and lower flight paths, wherein the upper flight path includes an exposed surface for receiving items. The sterilizing system includes a housing that is configured to at least partially cover the lower flight path. The sterilizing system also includes a motion sensor operatively associated with the belt. The motion sensor is operative to detect movement of the belt between the upper and lower flight paths. The sterilizing system further includes an ultraviolet light source positioned in the interior of the housing and operatively connected to the motion sensor. The ultraviolet light source is operative to emit ultraviolet light on the belt at the lower flight path to sanitize the belt in response the motion sensor detecting movement of the belt between the upper and lower flight paths and not emit ultraviolet light on the belt at the lower flight path in response to the motion sensor detecting no movement of the belt between the upper and lower flight paths.

In another aspect of the exemplary embodiment, a sterilizing system configured for sterilizing continuous loop conveyor belts having different widths, wherein each belt is movable between upper and lower flight paths, wherein the upper flight path includes an exposed surface for receiving items is provided. The sterilizing system includes a housing that is configured to at least partially cover the lower flight path. The sterilizing system also includes an ultraviolet light unit positioned in an interior of the housing that is operative to emit ultraviolet light on the surface of each of the belts at the lower flight path to sanitize the belt. The ultraviolet light unit is adjustable between a first configuration and at least a second configuration. The ultraviolet light unit is operative in the first configuration to emit light that extends across a belt of a first width from one end of the belt to the opposite end of the belt. The ultraviolet light unit is operative in the second configuration to emit light that extends across another belt of a second width from one end of the another belt to the opposite end of the another belt. The second width is different from the first width.

In still another aspect of the exemplary embodiment, a sterilizing system for sterilizing a continuous loop conveyor belt of a conveyor system, wherein the conveyor system includes a drive operatively connected to the conveyor belt, wherein the drive is operative to move the belt between upper and lower flight paths, wherein the upper flight path includes an exposed surface for receiving items is provided. The sterilizing system includes a housing that is configured to at least partially cover the lower flight path. The sterilizing system also includes an ultraviolet light source positioned in the interior of the housing. The ultraviolet light source is operative to emit ultraviolet light on the belt at the lower flight path to sanitize the belt. The housing includes first and second access panels. The first and second access panels are operative to selectively open and close at least one access opening in the housing. The first and second access panels overlap each other and removably attach to each other at least partially by a seal. The seal is operative to prevent ultraviolet light from being emitted through edges of the first and second access panels.

In still another aspect of the exemplary embodiment, a sterilizing system for sterilizing a continuous loop conveyor belt of a conveyor system, wherein the conveyor system includes a drive operatively connected to the conveyor belt, wherein the drive is operative to move the belt between upper and lower flight paths, wherein the upper flight path includes an exposed surface for receiving items is provided. The sterilizing system includes a housing that is configured to at least partially cover the lower flight path. The sterilizing system also includes an ultraviolet light source positioned in the interior of the housing. The ultraviolet light source is operative to emit ultraviolet light on the belt at the lower flight path to sanitize the belt. The sterilizing system includes a light shield operatively associated with the ultraviolet light, wherein the light shield is operative to be in a first position blocking a predetermined amount of ultraviolet light emitted by the ultraviolet light source from being on the belt, wherein the light shield is operative to be in a second position allowing the ultraviolet light emitted by the ultraviolet light source to be on the belt.

In still another aspect of the exemplary embodiment, a sterilizing system for sterilizing a continuous loop conveyor belt of a conveyor system, wherein the conveyor system includes a drive operatively connected to the conveyor belt, wherein the drive is operative to move the belt between upper and lower flight paths, wherein the upper flight path includes an exposed surface for receiving items is provided. The sterilizing system includes a housing that is configured to at least partially cover the lower flight path. The sterilizing system also includes an ultraviolet light source positioned in the interior of the housing. The ultraviolet light source is operative to emit ultraviolet light on the belt at the lower flight path to sanitize the belt. The sterilizing system also includes monitor circuitry, wherein the monitor circuitry is operative to monitor at least one device of one of the sterilizing system and conveyor system, wherein the monitored data may be communicated to an input/output port.

In still another aspect of the exemplary embodiment, a sterilizing system for sterilizing a continuous loop conveyor belt of a conveyor system, wherein the conveyor system includes a drive operatively connected to the conveyor belt, wherein the drive is operative to move the belt between upper and lower flight paths, wherein the upper flight path includes an exposed surface for receiving items. The sterilizing system includes a housing that is configured to at least partially cover the lower flight path. The sterilizing system also includes an ultraviolet light source positioned in the interior of the housing. The ultraviolet light source is operative to emit ultraviolet light on the belt at the lower flight path to sanitize the belt. The housing includes at least one access panel, wherein the access panel is operative to selectively open and close at least one access opening in the housing. An optical light sensor is operatively connected to the ultraviolet light source, wherein the optical light sensor is operative to cause power to the ultraviolet light source to be cut in response to the optical light sensor detecting a predetermined amount of light indicative of the access panel being removed.

DETAILED DESCRIPTION OF EXEMPLARY EMBODIMENTS

Figure 1:
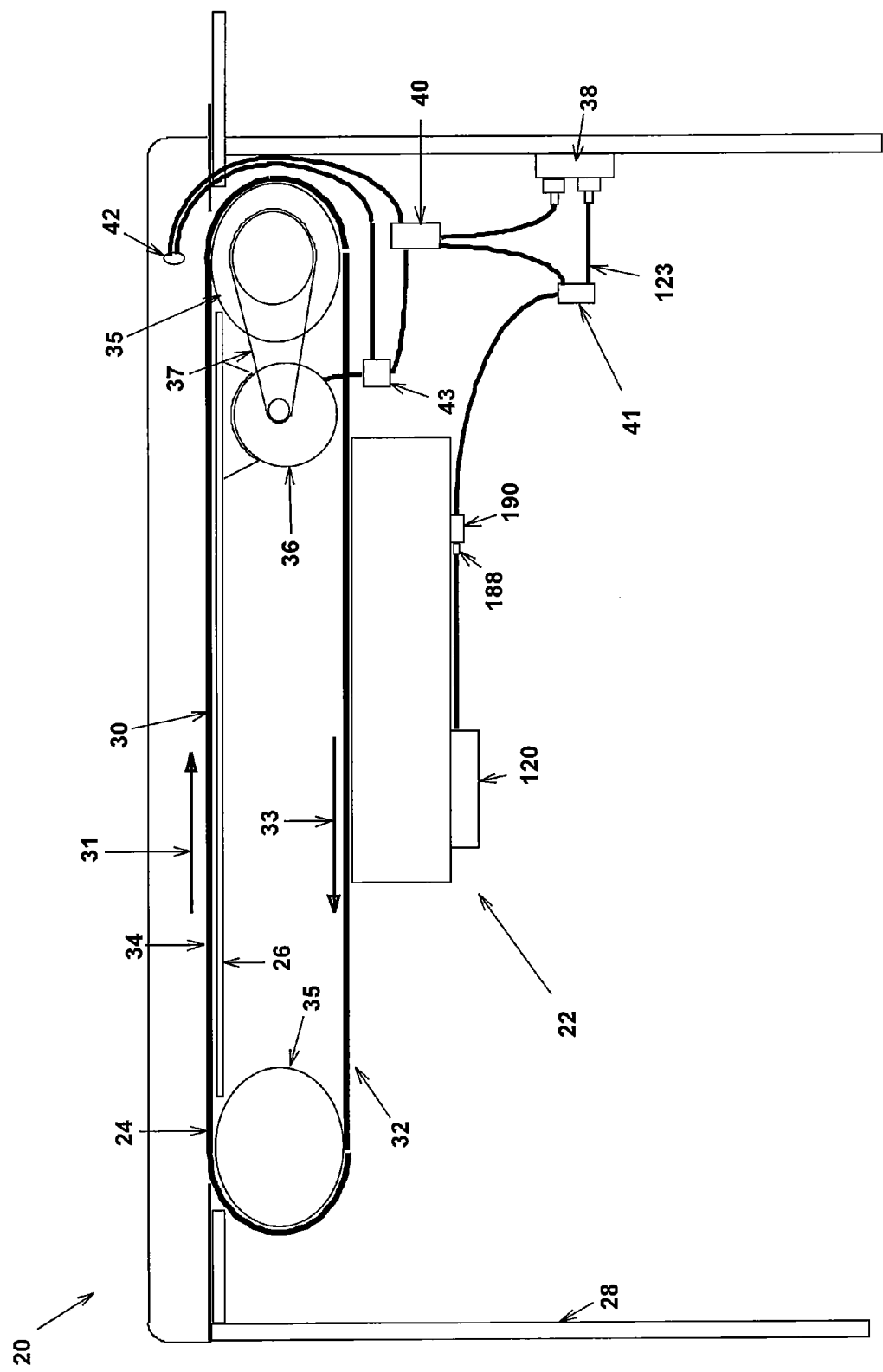
FIG. 1 is a schematic longitudinal sectional view of a conveyor belt system with portions removed to display the electrical power supply system for the conveyor belt system of an exemplary embodiment.
Figure 2:
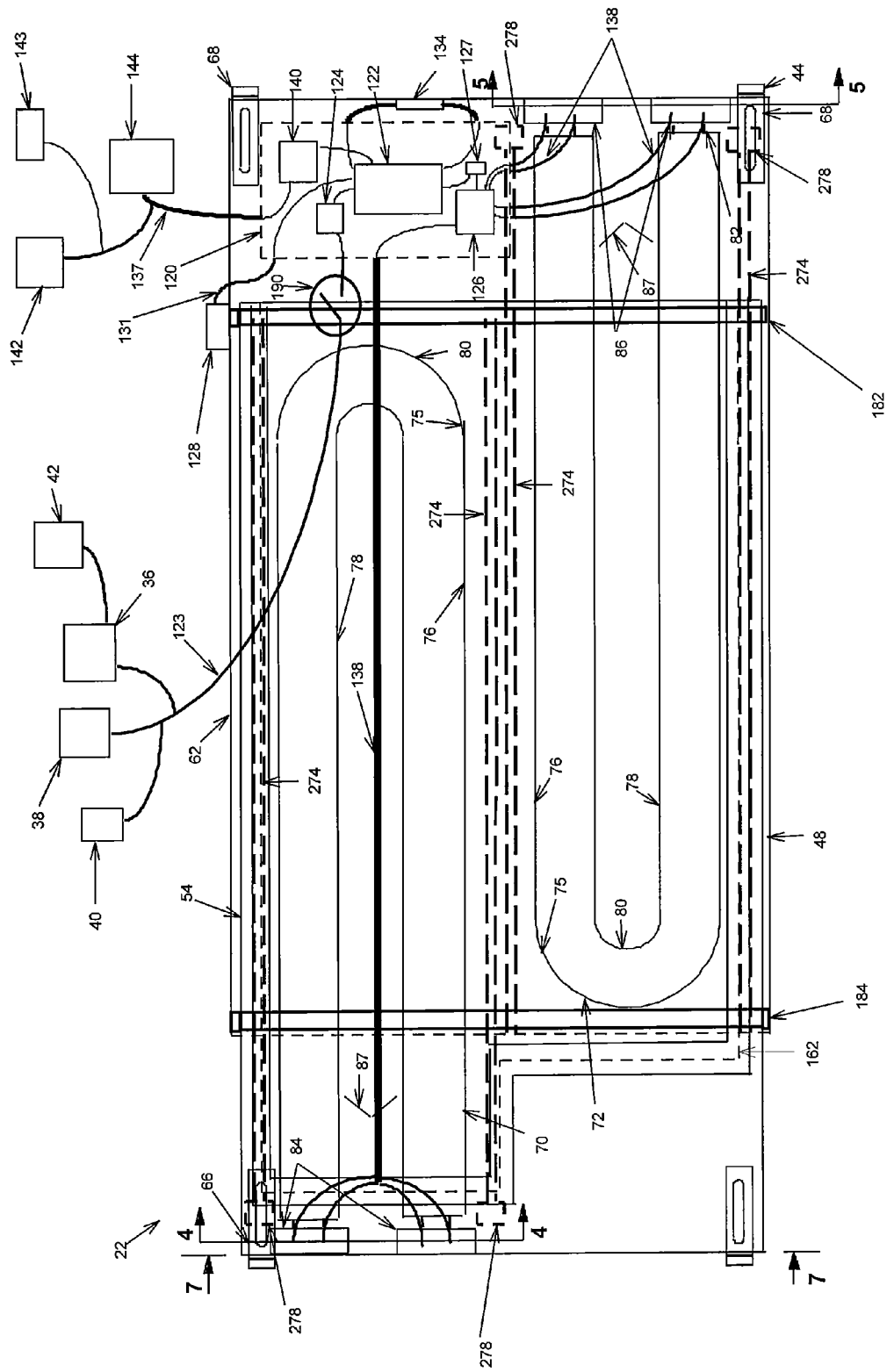
FIG. 2 is a schematic top view of the conveyor system with portions removed for illustrative purposes of an exemplary embodiment.
Figure 3:
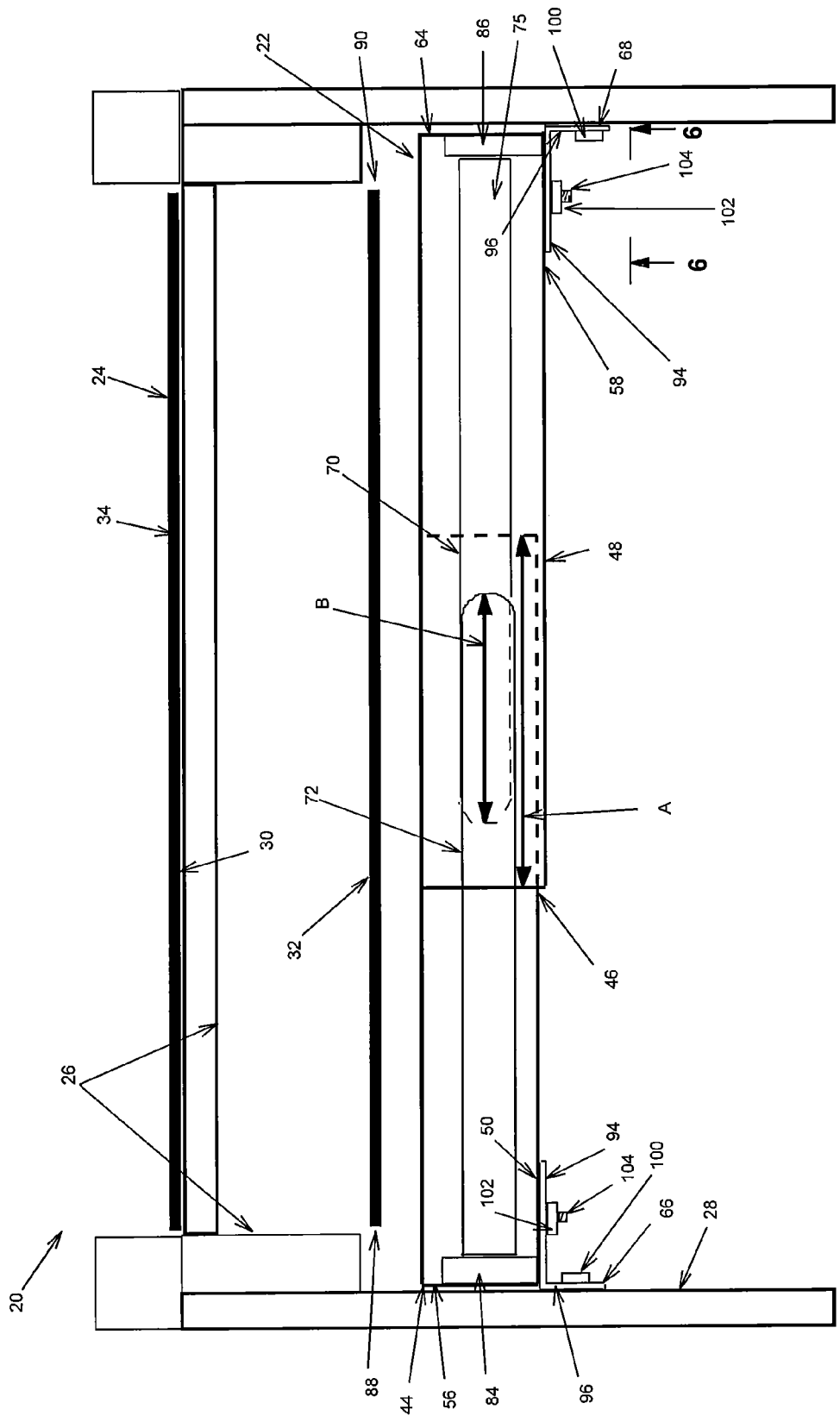
FIG. 3 is a schematic front end view of the exemplary conveyor system of FIG. 2 with portions removed for illustrative purposes.

FIGS. 1, 2 and 3 show a conveyor system 20 with a sterilizing system 22 constructed in accordance with an exemplary embodiment. The conveyor system 20 may be configured to transport items in a retail point of purchase, checkout stand or other place where goods are sold. For example, the conveyor system may be configured to transport groceries or other items in a grocery or other checkout stand. As depicted in FIGS. 1 and 3, the conveyor system 20 includes a continuous loop conveyor belt 24 that is supported on a frame 26. The frame 26 is fixedly supported by a stand 28. The conveyor belt 24 operates to move in the direction displayed by arrows 31 (for the upper flight path 30) and 33 (for the lower flight path 32) relative to the frame 26 between upper and lower flight paths 30, 32 of the conveyor system 20. The belt includes an exposed surface 34 facing upwardly at the upper flight path 30 that receives items. The conveyor belt may be support on each end by a roller 35 and pulley system 37 or other device for facilitating movement of the belt 24. At the lower flight path 32, this belt surface faces downwardly toward the ground. The rollers are rotatably driven by a drive such as a motor 36 (FIGS. 1 and 2) to move the conveyor belt 24 between the upper and lower flight paths 30, 32.

As shown in FIGS. 1 and 2, power source 38, such as an external source of AC power from a power outlet, supplies power to the conveyor system 20. The conveyor system 20 includes a main power switch 40 operatively connected to the power source that is operative to turn on the conveyor system 20 so that power may be to provide to the conveyor system 20. The conveyor system 20 may include a product sensor 42 that detects an item on the exposed surface 34 of the conveyor belt 24. The product sensor 42 is operatively connected to the motor control switch 43. When products are placed on the exposed surface 34 of the upper flight path 30 of the belt 24 the products will be transported towards the product sensor 42. When the product sensor detects a product on the belt, a signal is sent to the motor control switch 43 turning the motor 36 off stopping the advancement of the belt 24.

In operation, the conveyor system 20 is turned on by operation of the power switch 40 activating the advancement or movement in the directions 31, 33 of the belt 24 between the upper and lower flight paths 30, 32. The customer approaches a checkout stand and places his groceries or other item(s) on the exposed surface 34 of the upper flight path 30 of the belt 24 that advances the groceries or other item(s) towards the product sensor 42. When the product sensor 42 detects the item(s), it sends a signal to the motor control switch 43 operatively connected to the motor 36 to cause the motor 36 to stop advancing the conveyor belt 24 between the upper and lower flight paths 30, 32. The conveyor belt 24 may start automatically after the item(s) is removed from the exposed surface 34. Alternatively or in addition, the conveyor system 20 may be operated manually to control movement of the conveyor belt 24.

As seen in FIG. 3, the sterilizing system 22 includes a housing 44 that covers or at least partially covers the belt 24 at the lower flight or return path 32. The housing 44 may be made of a metal or any other material that has ferromagnetic properties. The housing 44 also includes an inner housing piece 46 and an outer housing piece 48. As depicted in FIGS. 2-5, the inner housing piece 46 includes a bottom wall 50 and upstanding front, rear and left side walls 52, 54, 56 extending from the bottom wall 50. The outer housing piece 48 includes a bottom wall 58 and upstanding front, rear, and right side walls 60, 62, 64 extending from the bottom wall 58. The outer housing piece 48 overlaps a portion of the inner housing piece 46 near the right end of the inner housing piece as viewed in FIGS. 2 and 3. In other words, the open end of the outer housing piece 48 at its left end slidably receives the portion of the inner housing piece 46 at its right end. This overlapping portion defines an expansion joint in which the inner housing piece and outer housing piece may move laterally relative to each other. The range of this movement is indicated by arrow A (FIG. 3). The expansion joint thus allows the width of the housing 44 to increase or decrease as indicated by the arrow A in order to match the width of the conveyor system 20. Left and right angle brackets 66, 68 mount the housing to the stand 28 and determine the range of the width of the housing 44. This will be explained below in more detail.

Figure 13:
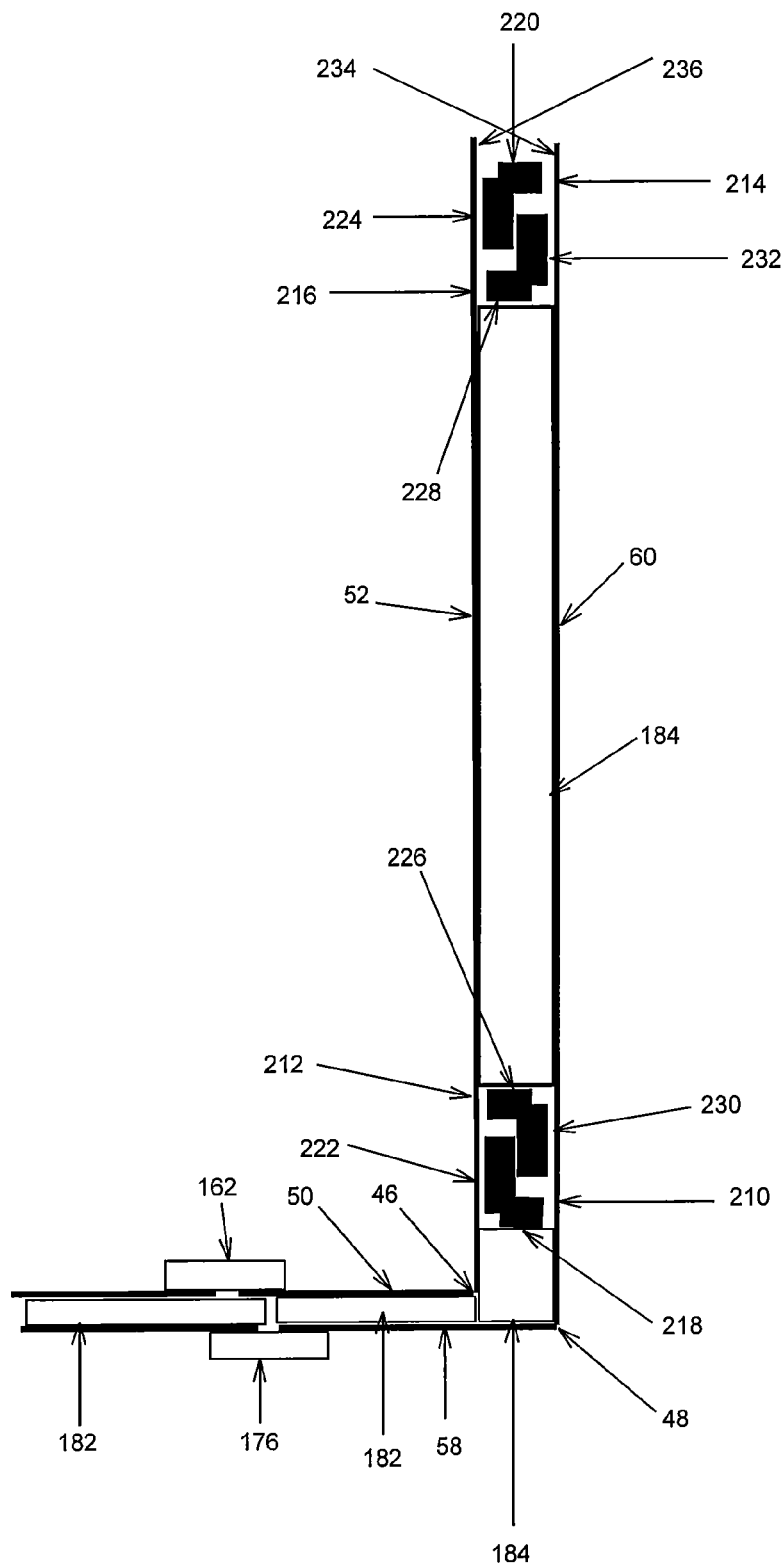
FIG. 13 is a schematic sectional view along line 13-13 of FIG. 7.

The exemplary embodiment of the width adjustable housing may include a dual set of opposing siding rails 210, 212, 214 and 216 as shown in FIG. 13. The sliding rails 210, 214 are permanently attached to inner surface 234 of the front wall 60 of the outer housing piece 48.

The lower rail 210 includes a base 218 that is attached proximal to the bottom wall 58 of the outer housing piece 48. The base 218 extends inward towards outer surface 236 of the front wall 52. Flange 222 is connected to the base 218 and extends upward. The base 220 of the upper rail 214 is permanently attached on the inner surface 234 proximal to the upper end of front wall 60 and extends inward towards the outer surface 236 of the front wall 52. Flange 224 is connected to the base 220 and extends downward. The base 226 of the lower rail 212 on the outer surface 236 is attached proximal to the bottom wall 50 of the inner housing piece 46 and extends outward towards the inner surface 234 of the front wall 60. Flange 230 is connected to the base 226 and extends downward. The upper rail 216 includes a base 228 that is permanently attached on the outer surface 236 proximal to the upper end of the front wall 52 and extends outward towards the inner surface 234 of the front wall 60 of the outer housing piece 48. Flange 232 is connected to the base 228 and extends upward.

Rail 210 slidably receives rail 212 and rail 214 slidably receives rail 216. When each of the rails 210, 212, 214 and 216 slidably receive its corresponding rail, as outlined above, the dual set of sliding rails will hold the inner housing piece 46 in position relative to the outer housing piece 48 such that there will not be any vertical movement between the inner and outer housings 46, 48 and the sterilizing system 22 will not sag in the middle.

Figure 17:
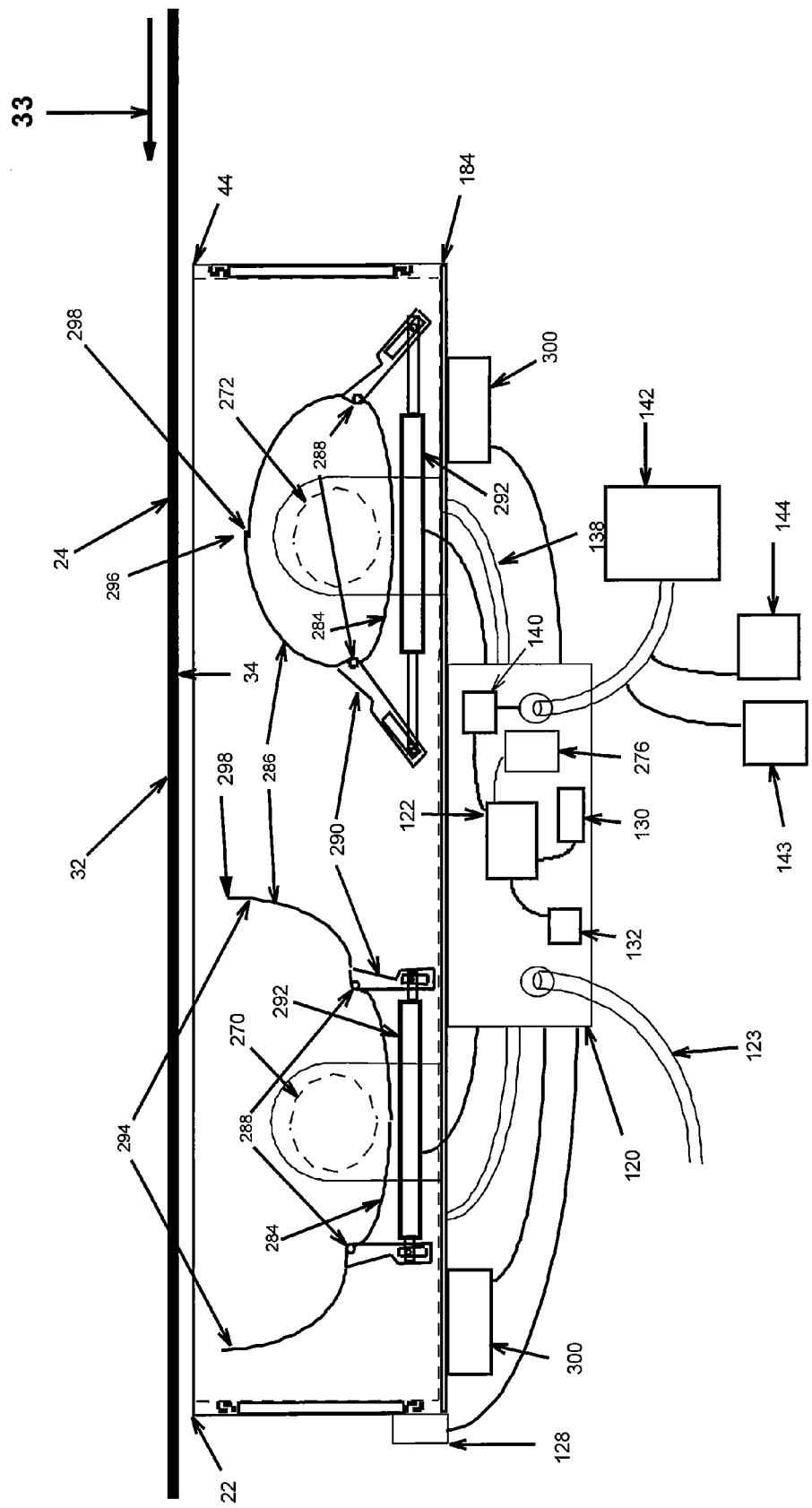
FIG. 17 is a schematic view as seen along line 16-16 of FIG. 16.

An alternative configuration of this exemplary embodiment may include one or more circulating fans 300 (FIGS. 7, 15, 17) designed and positioned to dissipate heat generated from the operation of the first and second light sources 70 and 72.

Figure 7:
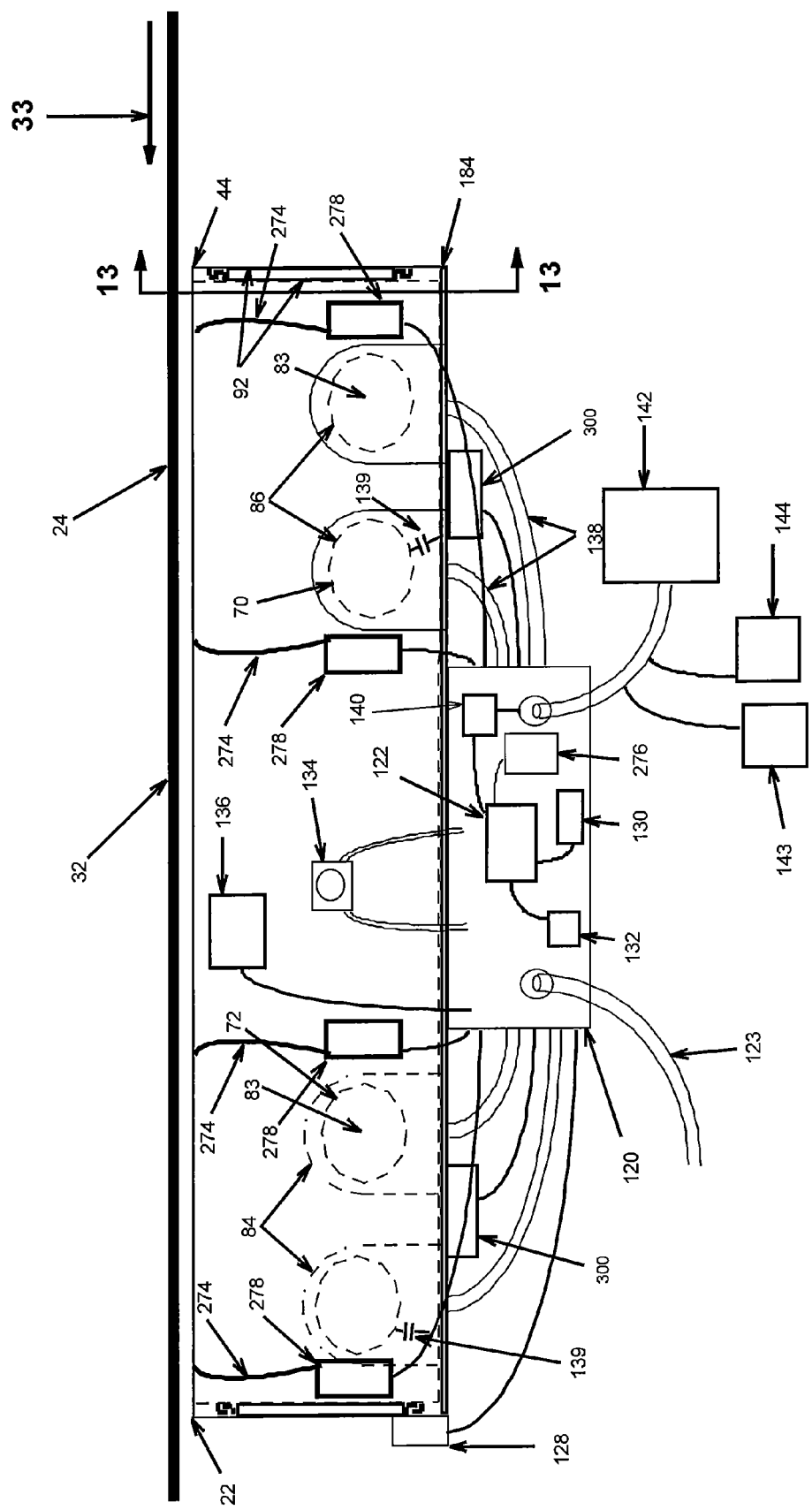
FIG. 7 is a schematic view as seen along line 7-7 of FIG. 2.

First and second ultraviolet light sources 70, 72 are positioned in the interior of the housing 44. Each light source is operative to emit or generate ultraviolet light with a single wavelength or multiple wavelengths within the wavelength range of 180 to 290 nm. Each ultraviolet light source may comprise mercury tubes, light emitting diodes (LEDs) or any other suitable ultraviolet light source. In this exemplary embodiment, each of the ultraviolet light sources is configured as an elongated u-shaped tube 75 as shown in FIG. 2. This exemplary embodiment depicts a configuration including two ultraviolet light sources 70, 72, however, other exemplary embodiments may accommodate less than or more than the two light sources depicted in this design. Each tube includes parallel leg portions 76, 78 and a curved bight portion 80. Alternatively, the portion 80 may be straight rather than curved in some exemplary arrangements. Each tube 75 is oriented such that the leg portions lie in a plane that is generally parallel to the belt surface facing the tube. Each tube is also oriented such that the longitudinal axis 83 of a leg of the tube is perpendicular to the belt movement in the direction 33 as depicted in FIG. 7. Electrical prongs 82 extend from the free end of each leg portion. The prongs 82 of the first ultraviolet light source 70 are inserted into bulb connectors or electrical sockets 84. The sockets 84 are mounted to the bottom wall 50 of the inner housing piece 46 at the left side wall 56 of the inner housing piece 46. The prongs 82 of the second ultraviolet light source 72 are inserted into bulb connectors or electrical sockets 86. The sockets 86 are mounted to the bottom wall 58 of the outer housing piece 48 at the right side wall 64 of the outer housing piece 48.

The first and second ultraviolet light sources 70, 72 are spaced from one another along the lower flight path 32. The ultraviolet light sources 70, 72 are positioned to collectively emit ultraviolet light that irradiates across the surface of the belt 24 with the emitted light starting from one end 88 of the belt and ending at the other end 90 of the belt 24. In essence, the light shines only on the surface of the belt 24 but extends across the belt surface to ensure that the entire belt surface passes over the light sources 70, 72 and receives ultraviolet radiation to sterilize the belt surface. Alternatively, the ultraviolet light sources 70, 72 may be configured to emit light that extends across the belt 24 and beyond the ends 88, 90 of the belt 24. The ultraviolet light sources 70, 72 may be so positioned so as not to interfere from each other. An ultraviolet reflective lining or coating 92 (FIG. 7) is applied on the interior surface of the housing to maximize ultraviolet exposure on the conveyor belt 24. The housing 44 is configured to completely contain the light sources 70, 72 and prevent ultraviolet light from escaping. Additionally, reflectors 87 (FIG. 2) may be installed on the inner and outer housing 46, 48 to ensure that sufficient ultraviolet light is incident across the entire width of the conveyor belt 24 including the ends 88, 90.

Since the first light source 70 is fixed to the inner housing piece 46 and the second light source 72 is fixed to the outer housing piece 48, the first and second light sources 70, 72 may be movable in their longitudinal direction relative to each other at selected positions. Each of these positions corresponds to an emission of light of a particular width. This allows the width of the emitted light to be adjusted in order to accommodate belts that have different widths. The range of the adjusted widths is determined by the configuration of the conveyor system 20 and the conveyor stand 28. Upon adjusting the sterilization system to the appropriate width, the angle brackets 66, 68 are fastened to the conveyor stand 28 and locked in place with the locking nuts 102. In particular, referring to FIGS. 3 and 6, each of the angled brackets 66, 68 is L-shaped and includes a top plate 94 and a side plate 96. The top plate 94 includes a slot 98 (FIG. 6) that extends longitudinally with respect to the top plate 94. The side plates 96 of the left brackets 66 are mounted to the left side of the conveyor stand 28 by attachment screws 100. The top plates 94 of the left brackets 66 are mounted to the bottom wall 50 of the inner housing piece 46 by locking nuts 102 and threaded bolts 104. Specifically, for each of the left brackets 66, the bolt 104 extends through the bottom wall 50 and the slot 98 of the top plate 94. The locking nut 102 is then threadibly turned on the bolt 104 to fix the bottom wall 50 of the inner housing piece 46 to the bracket 66.

Likewise, the side plates 96 of the right brackets 68 are mounted to the right side of the conveyor stand 28 by attachment screws 100. The top plates 94 of the right brackets 68 are mounted to the bottom wall 58 of the outer housing piece 48 by locking nuts 102 and threaded bolts 104. Specifically, for each of the right brackets 68, the bolt 104 extends through the bottom wall 58 and the slot 98 of the top plate 94. The locking nut is then threadibly turned on the bolt 104 to fix the bottom wall 58 of the outer housing piece 48 to the bracket 68.

To adjust the width of the light emitted by the lights sources 70, 72, the locking nuts 102 are loosened from their respective bolts 104. Then, the left and right angle brackets 66, 68 are securely fastened to the conveyor stand 28 with the attachment screws 100. Upon fastening the angle brackets 66 and 68 to the conveyor stand 20, the width of the light emitted by the light sources 70, 72, may be expanded to radiate the entire width of the exposed surface 34 to its width permitted by the bolts 104 and slots 98. Since the first light source 70 is fixed to the inner housing piece 46 and the second light source 72 fixed to the outer housing piece 48, the light sources may be moved relative to each other along the slots 98. After the light sources 70, 72 are moved to the desired position, the locking nuts are then threadily fastened on their respect bolts and turned and tightened until the housing 44 is fixed or lock to the brackets. The arrow B shows the overlapping region or range of movement of the first and second light sources 70, 72 relative to each other.

Figure 10:
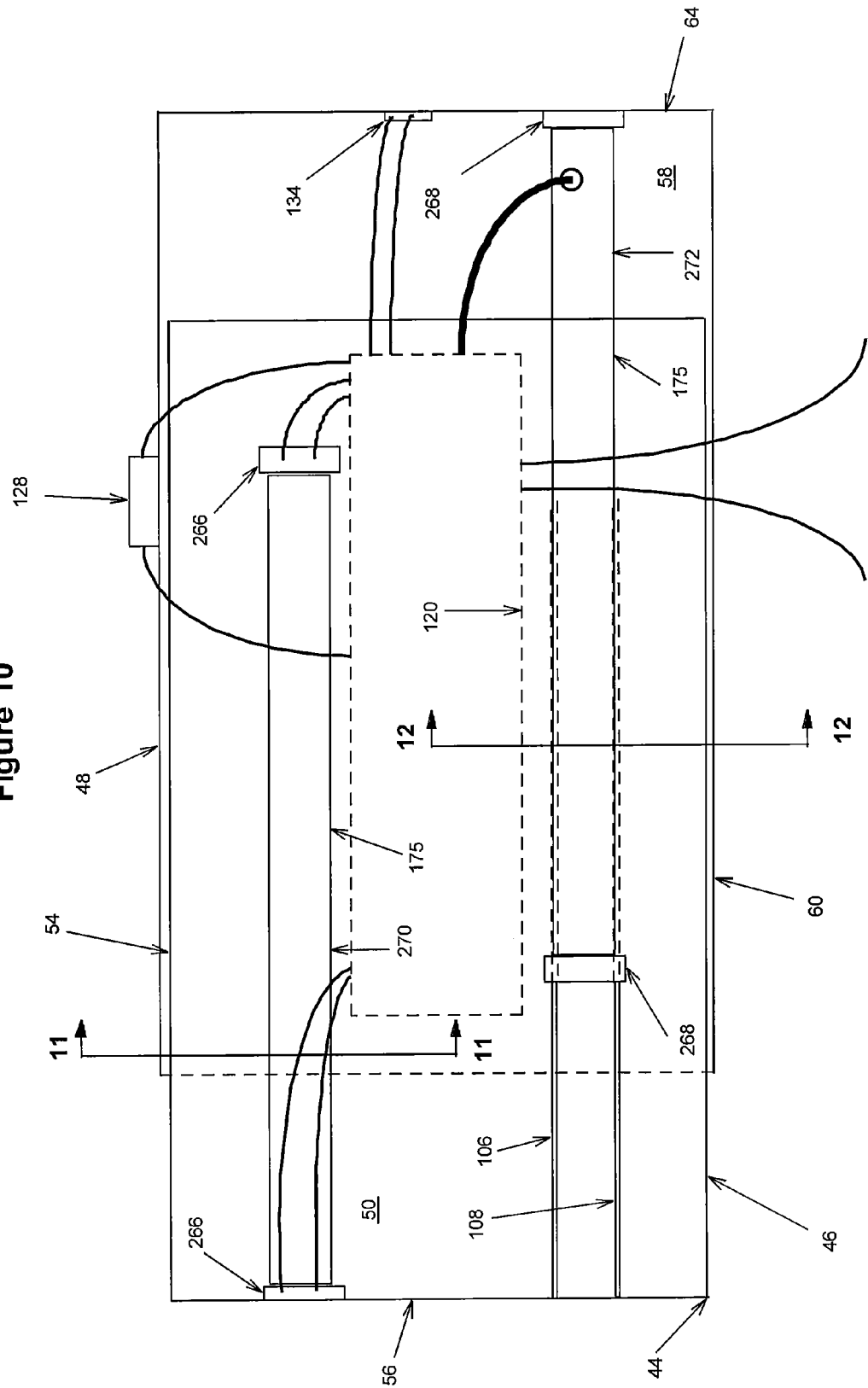
FIG. 10 is a schematic top view of the sterilizing system of FIG. 2 showing an alternative exemplary arrangement of the ultraviolet light sources.
Figure 11:
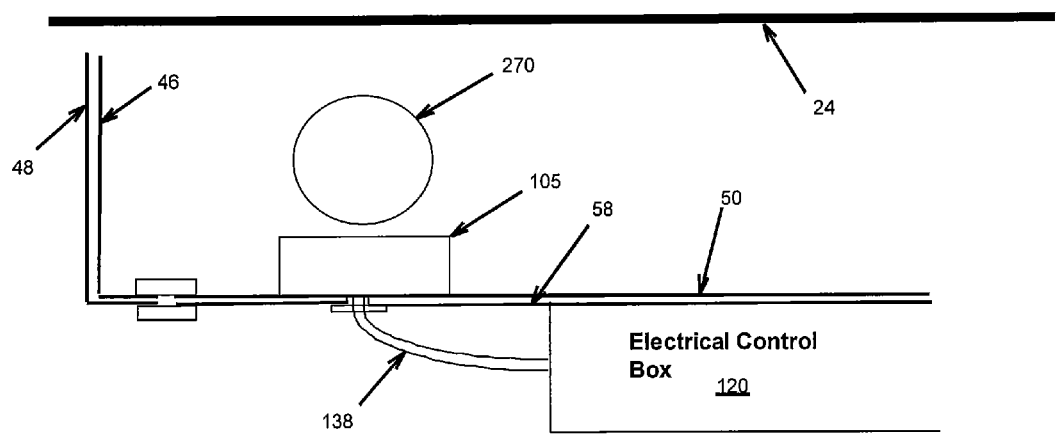
FIG. 11 is a schematic sectional view along line 11-11 of FIG. 10.
Figure 12:
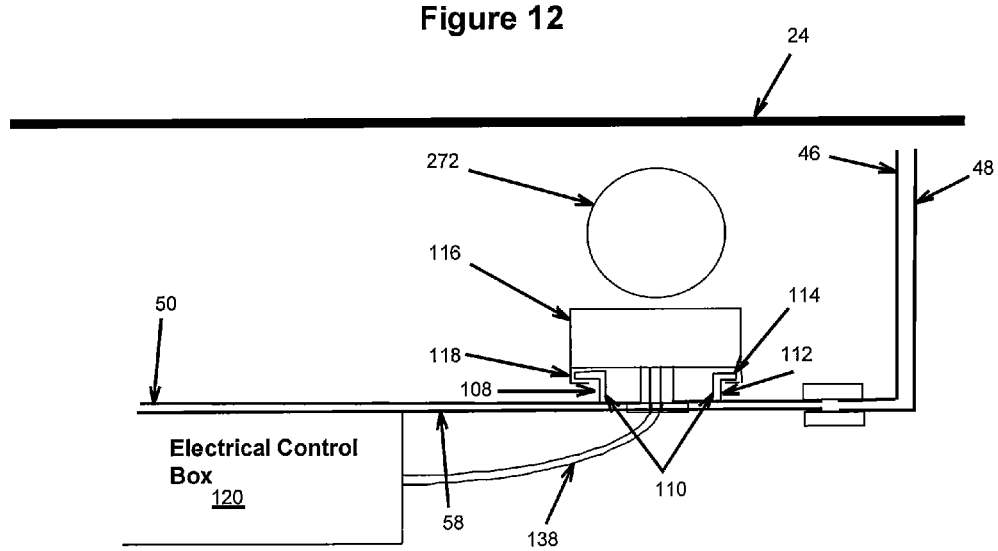
FIG. 12 is a schematic sectional view along line 12-12 of FIG. 10.

An alternative exemplary arrangement of first and second ultraviolet light sources 270, 272 is shown in FIGS. 10-12. In this arrangement, each of the tubes 175 of the light sources 270, 272 may be straight or I-shaped. The first light source 270 is mounted to fixture 105, which in turn is mounted to the the bottom wall 50 of the inner housing piece 46. Each of the ends of the first light source 270 is electrically coupled to an electrical socket 266. One electrical socket 266 is mounted on the left side wall of the inner housing piece 56, and the other electrical socket 266 mounted near the right end of the inner housing piece 46. The second light source 272 is mounted to a fixture 116. Each of the ends of the second light source 272 is mounted to an electrical socket 268. One electrical socket 268 of the second light source 272 is mounted to the bottom wall 58 of the outer housing piece 48 on the right side wall of the outer housing piece 64 and the other electrical socket 268 is slidably mounted to a sliding support bracket 106, which is mounted to the bottom wall 50 of the inner housing piece 46. Specifically, as depicted in FIG. 12, the support bracket 106 includes a track 108 with two rails 110. Each rail 110 includes a base 112 that is connected at its upper end to a flange 114 that extends outwardly. The fixture 116 includes two L-shaped legs 118. Each leg 118 extends downwardly and inwardly to define a channel. Each channel slidably receives the flange 114 of its corresponding rail 110. The sliding support bracket 106 extends from the left side wall 56 to near the right end of the inner housing piece 46 as seen in FIG. 10. The second light source 272 slides along the track 108 of the support bracket 106 when the inner and outer housing pieces 46, 48 move relative to each other to adjust the width of the light emitted.

Referring to FIGS. 1 and 2, the sterilizing system 22 includes an electrical control box 120. The electrical control box 120 is electrically coupled via an electrical cord 123 to the power source 38 and mounted to the bottom wall 58 of the outer housing piece 48. The electrical control box 120 is configured to direct and control power from the power source 38 to various devices of the sterilizing system 22. The electrical control box 120 may include control circuitry 122 or a controller for controlling devices based on certain conditions. A transformer 124 may be provided in the electrical control box 120 to step down the supply voltage to a level suitable for low voltage circuits (e.g. sensors) coupled to it. Other transformers may be included in the system. Referring to FIG. 2, the electrical control box 120 directs power from the power source 38 to the electrical sockets 84, 86 (for U shaped bulbs 75) or 266, 268 (for I shaped bulbs 175) to supply power via lines 138 to the ultraviolet light sources 70, 72. A ballast 126 may be coupled to the light sources 70, 72. The ballast 126 is operative to drive the ultraviolet light sources 70, 72.

A conveyor motion sensor 128 may be electrically coupled via a power signal wire 131 to the electrical control box 120. The motion sensor 128 is operatively associated with the belt and is operative to detect movement of the belt 24 between the upper and lower flight paths 30, 32. The motion sensor 128 may be an optical sensor or a sensor that operates via mechanical connection of the belt or roller. Other suitable motion sensors may also be used instead. The motion sensor 128 is operatively connected to the ultraviolet light sources 70, 72 through the control circuitry 122. The control circuitry 122 causes the ultraviolet light sources 70, 72 to turn on and emit ultraviolet light on the belt at the lower flight path 32 in response to the motion sensor 128 detecting movement of the belt 24 between the upper and lower flight paths 30, 32.

Specifically, the motion sensor 128 outputs a signal indicative of the belt 24 moving between the upper and lower flight paths 30, 32 to the control circuitry 122 which in turn causes the ultraviolet light sources 70, 72 to turn on and emit ultraviolet light on the belt at the lower flight path 32. When the movement of the belt 24 stops, the motion sensor 128 outputs a signal to the control circuitry 122, which in turn causes the ultraviolet light sources 70, 72 to turn off and not emit ultraviolet light on the belt 24. The motion sensor 128 is independent of the power controls of the conveyor system 20. Thus, existing conveyor belt systems would not need to be modified in order to connect, for example, an on/off switch for the ultraviolet light in the existing control circuitry of the conveyor belt system.

Alternatively, the sterilizing system 22 could be activated in other ways. For example, the sterilizing system 22 could be activated by incorporating a sterilizing system, control switch 41 that receives a power signal in response to the power switch 40 turning on. This would allow the sterilizing system to completely power down including the motion sensor 128 when the conveyor system 20 is turned off.

Alternatively the ultraviolet light sources could be activated by a switch wired into the product sensor 42 rather than the motion sensor 128. In this example, the product sensor 42 outputs a signal indicative of the belt 24 moving between the upper and lower flight paths 30, 32 to the control circuitry 122 which in turn causes the ultraviolet light sources 70, 72 to turn on and emit ultraviolet light on the belt at the lower flight path 32. The light sources could also be wired to the power source of the motor 36 rather than the motion sensor 128 or the product sensor 42. In this example, the motor 36 outputs a signal indicative of the belt 24 moving between the upper and lower flight paths 30, 32 to the control circuitry 122 which in turn causes the ultraviolet light sources 70, 72 to turn on and emit ultraviolet light on the belt at the lower flight path 32

Often the motor 36 (or motors) that moves the belt turns on and off frequently and typically is not running for more than one or two seconds. This action causes the ultraviolet light sources to switch on and off frequently thereby causing premature degradation to the ultraviolet light source. In addition, the conveyor system 20 may not be on long enough which results in the light sources not being charged to full power which in turn results in providing insufficient intensity of ultraviolet radiation to sterilize the conveyor belt surface. To solve this problem, a delay switch 130 (FIG. 7) is provided in the sterilizing system 22 to keep the light sources 70, 72 activated for an adequate time even after the belt 24 stops moving. In one exemplary embodiment, the delay switch 130 is incorporated into the electrical control box 120 and operatively connected to the ultraviolet light sources 70, 72 and motion sensor 128 via the control circuitry 122 in the electrical control box 120. When the motion sensor 128 detects that the belt 24 has stopped moving between the upper and lower flight paths 30, 32, the motion sensor 128 outputs a signal indicative of this condition to the delay switch 130 via control circuitry 122 in the control box 120. The delay switch 130 delays for a predetermined time the sending of this signal to the ultraviolet light sources that turns them off. The predetermined time may be set at time that the belt 24 will be adequately irradiated.

A power reduction switch 132 (FIG. 7) may also be provided. The power reduction switch 132 is operative to reduce the power output and hence, light intensity of the ultraviolet light sources 70, 72 by a predetermined amount after the belt 24 has remained motionless for a first predetermine time. In one exemplary embodiment, the power reduction switch 132 is operatively connected to the light sources 70, 72 and motion sensor 128 via control circuitry 122. When the motion sensor 128 detects that the belt 24 has stopped moving between the upper and lower flight paths 30, 32, the motion sensor 128 outputs a signal indicative of this condition to the power reduction switch 132 via control circuitry 122 in the control box 120. After the first predetermined time has lapsed upon receipt of this signal, the power reduction switch 132 reduces the power output of the ultraviolet light sources 70, 72. The ultraviolet light sources 70, 72 may turn off or deactivate completely after the belt has remained motionless for a second predetermined time, which is greater than the first predetermined time. Alternatively, the ultraviolet light sources may also be automatically powered down or their power reduced when the conveyor system is turned off via the main power switch 40 described above.

Alternatively or in addition, an ultraviolet light shield 274 may be provided. The ultraviolet light shield 274 is controlled by a light shield switch 276 that sends a signal to the ultraviolet light shield motor 278, which in turn rotates the ultraviolet light shield 274 such that the light shield would block all or most of the ultraviolet radiation from intersecting or shining on the exposed surface 34 of the conveyor belt 24.

Figure 14:
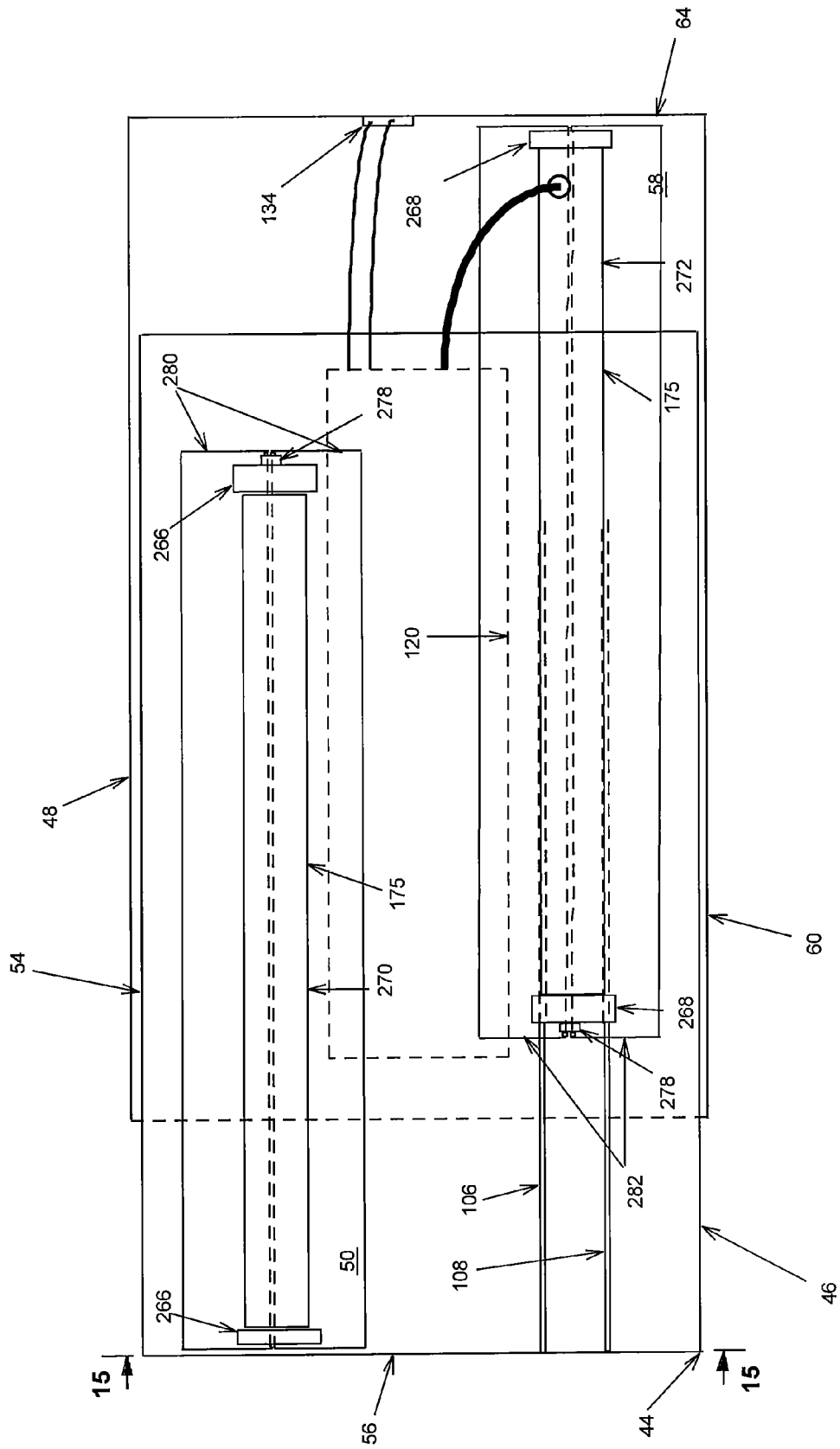
FIG. 14 is a schematic top view of the sterilizing system of FIG. 2 showing an alternative exemplary arrangement of the ultraviolet light sources with light shields.
Figure 15:
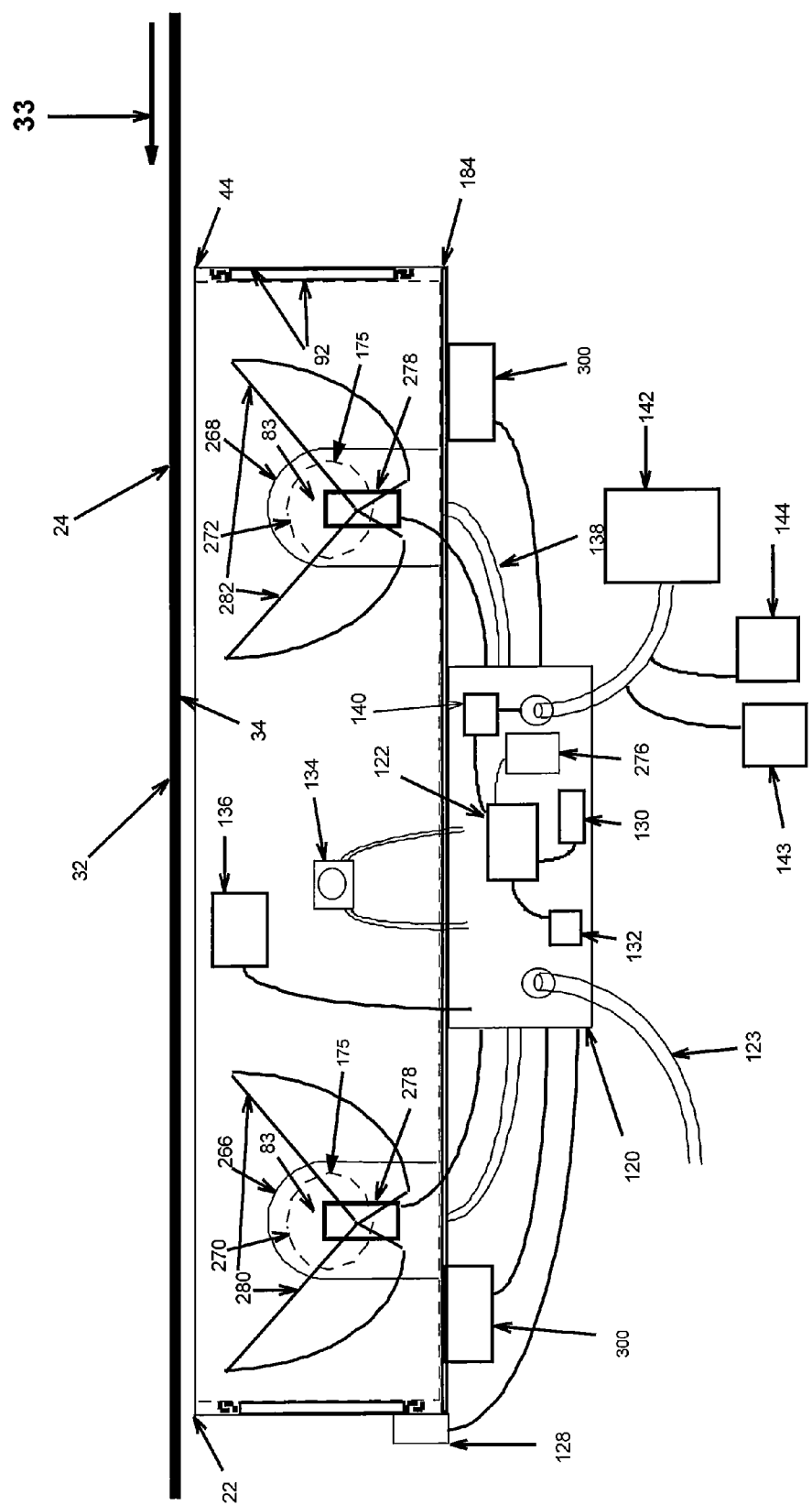
FIG. 15 is a schematic view as seen along line 15-15 of FIG. 14.
Figure 16:
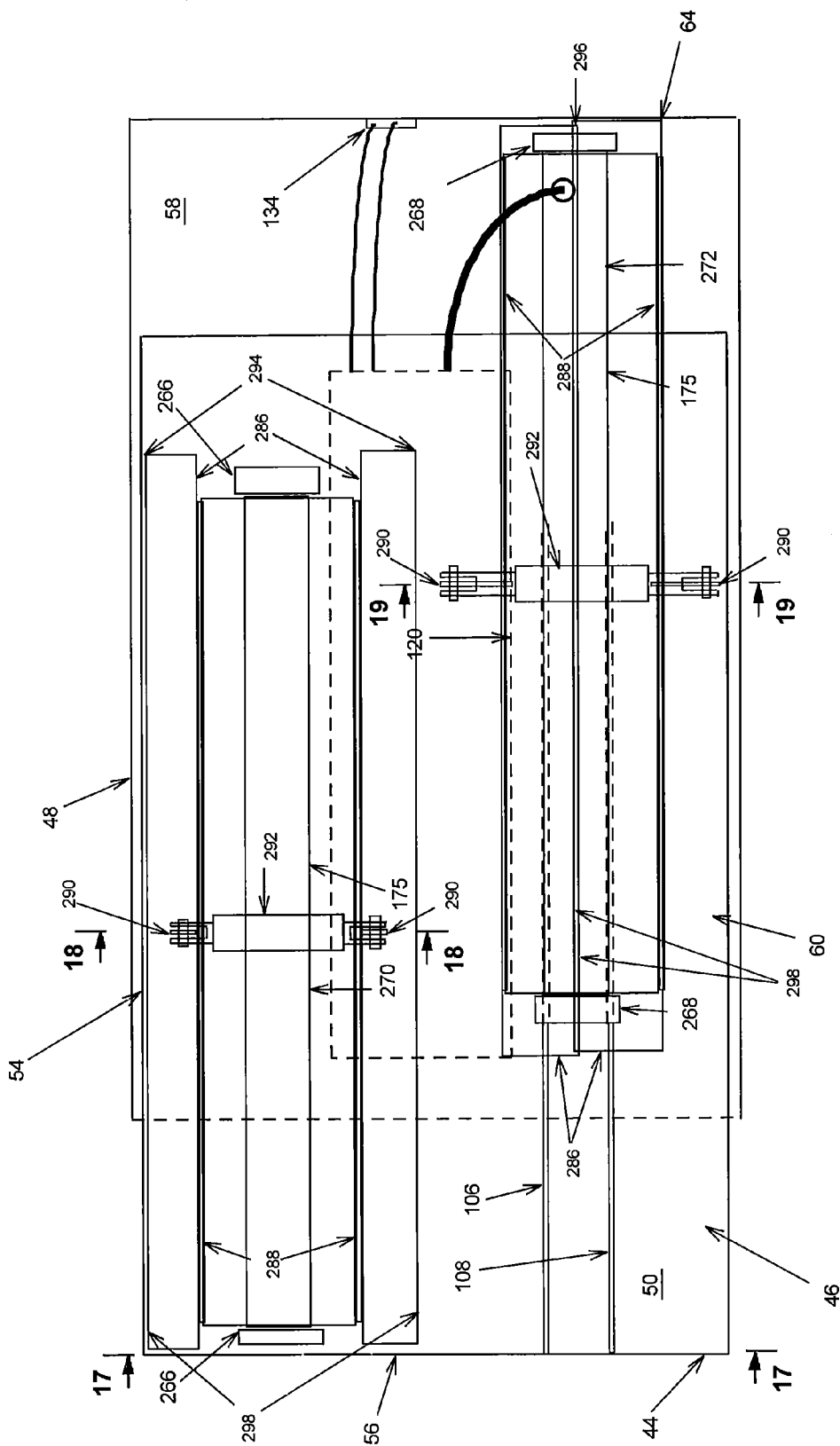
FIG. 16 is a schematic top view of the sterilizing system of FIG. 2 showing another alternative exemplary arrangement of the ultraviolet light sources with light shields.

FIGS. 14 and 15 show an exemplary arrangement in which the ultraviolet light shields may comprise first and second pivoting parabolic light shields 280 and 282 around single I shaped light tube 175. In this arrangement, the pivoting parabolic light shields are controlled by a light shield switch 276 that sends a signal to the ultraviolet light shield motor 278, which in turn rotates the first and second parabolic light shields 280, 282 such that the light shield would block all or most of the ultraviolet radiation from intersecting or shining on the exposed surface 34 of the conveyor belt 24.

FIGS. 16-19 show another exemplary arrangement in which the first and second pivoting parabolic light shields 280 and 282 may be constructed in three (or more) pieces. In particular, each shield includes a bottom fixed shield portion 284 and two rotating shield portions 286 on opposite sides of the fixed shield portion 284. The rotating shield portions 286 are also located on opposite sides of the light tube 175. Each of the rotating shield portions 286 pivots on a respective light shield hinge 288 provided on the fixed shield portion and is controlled by a respective light shield actuator arm 290. Each light shield actuator arm 290 is operatively connected to a light shield actuator 292 capable of positioning the rotating light shield portion between a fully open position 294 and a closed position 296. The actuator 292 may be a mechanical motor, solenoid, spring, magnetic or other device capable of repositioning the rotating light shield portions 286. The actuators 292 are controlled by a light shield switch 276 that sends a signal to the actuator 292, which in turn pushes or pulls the light shield actuator arms 290 inwardly or outwardly.

Figure 18:
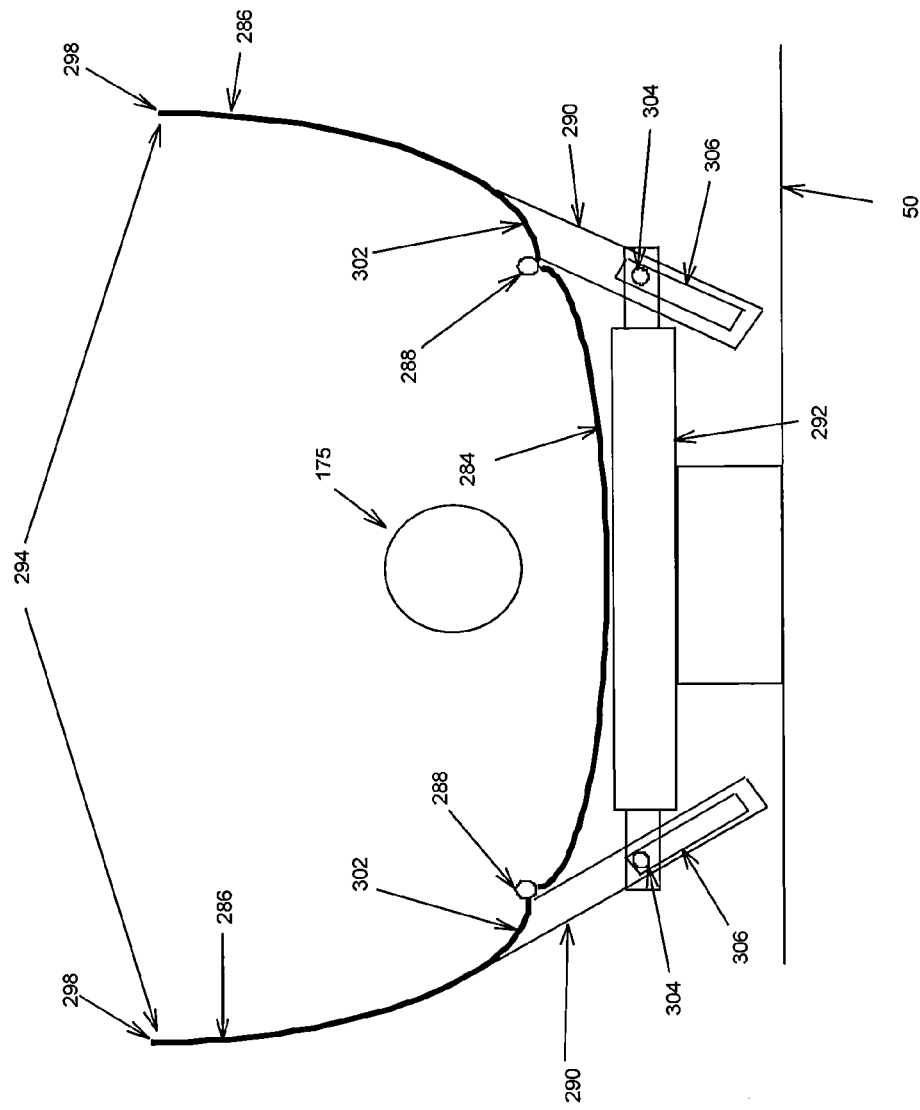
FIG. 18 is a schematic view as seen along line 17-17 of FIG. 16.
Figure 19:
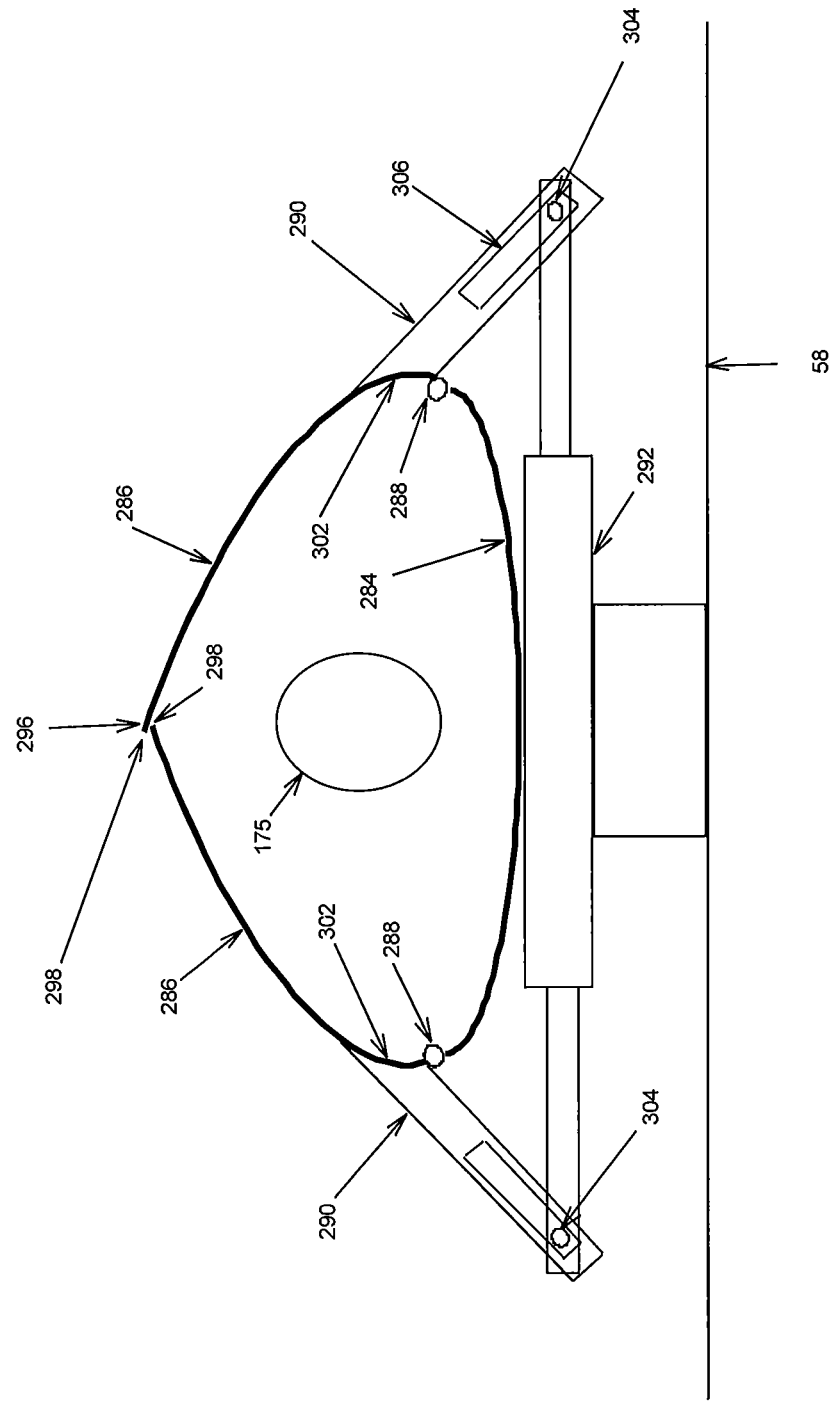
FIG. 19 is a schematic view as seen along line 19-19 of FIG. 16.

Referring to FIGS. 18 and 19, each light shield actuator arm is permanently attached (screws, bolt or welded) to its respective rotating light shield portion at shield portion area 302, which is located upwardly adjacent the light shield hinge 288. The light shield actuator arm 290 is also movably connected to the actuator 292 via a pivot pin 304. The pivot pin 304 slides along a slot 306 cut into the actuator arm 290 during inwardly and outward movement of the actuator arm 290. When the actuator 292 extends (moves outwardly), the outward force is transferred from the actuator 292 to the pivot pin 304 to the actuator arm 290 below the light shield hinge 288. Since the actuator arm 290 is permanently attached to the rotating light shield portion 286, the actuator arm 290 and the rotating light shield portion 286 act as a single unit that pivots on the light shield hinge 288 in the middle. When the lower end of the actuator arm 290 is pushed outwardly, the rotating light shield portion 286 must pivot inwardly in the opposite direction on the light shield hinge 288. Since the actuator 292 in this embodiment is fixed and the actuator 292 retracts (moves in) or extends (moves out) along a horizontal axis, the distance between the pivot pin 304 on the actuator and the shield portion area 302 increases as the actuator extends (moves outwardly) and decreases as the actuator 292 retracts (moves inwardly). Hence, the pivot pin 304 can slide back and forth along the slot 306 to accommodate the change in distance between the pivot pin 304 on the actuator and the point 302.

Thus, when the lower end of the light shield actuator arms 290 are pushed outwardly, the rotating light shield portions 286 pivot inwardly about the light shield hinge 288 such that the outer edge 298 of each of the rotating light shield portions 286 come together above the first and/or second light sources 270 and 272. In this position (as illustrated by the right light shield 282 of FIGS. 17 and 19), the light shield would block all or most of the ultraviolet radiation from intersecting or shining on the exposed surface 34 of the conveyor belt 24. When the lower end of the light shield actuator arms 290 are pulled inwardly, the rotating light shield portions 286 pivot outwardly about the light shield hinge 288 such that the outer edge 298 of each of the rotating light shield portions 286 separate to their fully open position (as illustrated by the left light shield 280 of FIGS. 17 and 18). This allows the ultraviolet radiation to intersect or shine onto the exposed surface 34 of the conveyor belt 24.

In one exemplary embodiment, the light shield switch 276 is operatively connected to the light shield motor 278 and motion sensor 128 via control circuitry 122. When the motion sensor 128 detects that the belt 24 has stopped moving between the upper and lower flight paths 30, 32, the motion sensor 128 outputs a signal indicative of this condition to the power reduction switch 132 via control circuitry 122 in the control box 120. After the first predetermined time has lapsed upon receipt of this signal, the power reduction switch 132 reduces the power output of the ultraviolet light sources 70, 72. After a second predetermined time, which is greater than the first predetermined time, has lapsed upon receipt of this signal, the light shield switch 276 activates the light shield motor 278 to rotate the ultraviolet light shield 274 reducing the ultraviolet light intensity incident on the exposed surface 34 of the conveyor belt 24. The ultraviolet light sources 70, 72 may turn off or deactivate completely after the belt has remained motionless for a third predetermined time, which is greater than the second predetermined time.

At any time during the first, second or third predetermined times, when the motion sensor 128 detects that the belt 24 begins moving between the upper and lower flight paths 30, 32, the motion sensor 128 outputs a signal indicative of this condition to the control circuitry 122 that sends a signal to the power reduction switch 132 and the light shield switch 276 ensuring that the light shield is deactivated and the light sources 70, 72 are returned to full power.

Figure 6:
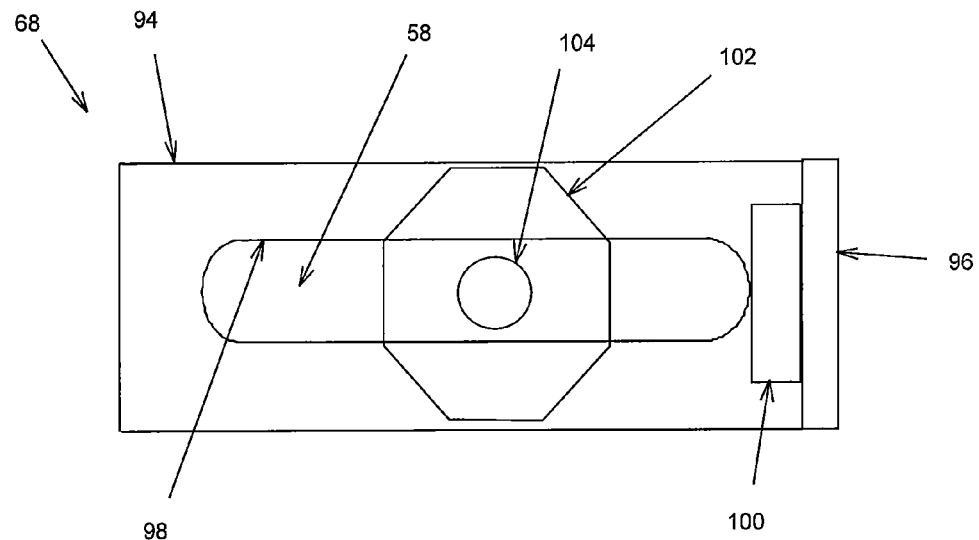
FIG. 6 is a schematic view along line 6-6 of FIG. 3.

As seen in FIG. 6, an ultraviolet light sensor 134 is electrically coupled to the electrical control box 120. The ultraviolet light sensor 134 is operative to sense the intensity of the ultraviolet light emitted by the light sources 70, 72. A contamination sensor 136 may also be electrically connected to the control box 120. The contamination sensor 136 is operative to detect dirt, liquid, or biological contaminant. This sensor 136 may operate via an optical, magnetic, electrical or any other form of remote sensing. The contamination sensor 136 may send data to a display screen 144 to notify the operator that a sterilization cycle is needed. Alternatively or additionally, the contamination sensor 136 may incorporate a warning device to notify the operator that sterilization is needed. The notification device could include lights or an audible alarm. The contamination sensor may also include control circuitry that causes the conveyor belt to stop until the contaminated area is radiated by the ultraviolet lights sources for a sufficient length of time to sterilize that section of the conveyor belt. The sterilizing system 22 may include a timer that activates the ultraviolet lights and the conveyor belt motor automatically to complete one or more decontamination cycles. An on/off override switch may be included to activate a complete timed treatment cycle. Capacitors schematically indicated at 139 may be coupled to the light sources or other devices in the systems to, for example, limit the amount of current to the device.

Monitor circuitry 140 may be provided in the electrical control box 120 to monitor the conditions of the devices or system in general. For example, the monitor circuitry 140 may measure the power drawn on various devices to monitor energy efficiency. This information may be used to determine the need for servicing or replacing devices, since devices such as ballasts draw more power as they begin to fail. The monitor circuitry 140 may include a computer chip or other electronic circuitry that can collect, transmit, and store data related to devices or the overall system functionality. The monitored data may be communicated via wireless or a line 137 from the control box 120 to an input/output (IO) port 142 (FIG. 7), wireless transmitter 143, or to an output device such as a display screen 144 (FIG. 2). Other output devices such as indicator lights or an audio device may instead be use. The display screen 144 may, for example, be part of personal computer (e.g. laptop, desktop, etc.), cell phone, personal digital assistant, an iPod®, iPhone®. The display screen 144 may have access to a website that receives the monitored data. The monitor circuitry may monitor the output of the ultraviolet light sensor and send data on the intensity of the light to the display screen. For example, the display may include a bar graph displaying the percentage of the intensity or the percentage remaining for the life of the lights.

The monitor circuitry 140 may monitor other devices. For example, the monitor circuitry may monitor the functioning of the on/off power switch 40 that turns on and off the power to the system. The monitor circuitry 140 may monitor the power drawn on the light sources 70, 72. The monitor circuitry 140 may monitor the functioning of the motion sensor 128. The monitor circuitry 140 may monitor the power drawn on the ballast, capacitors or transformers. The monitor circuitry 140 may monitor the functionality of the delay switch 130.

Figure 8:
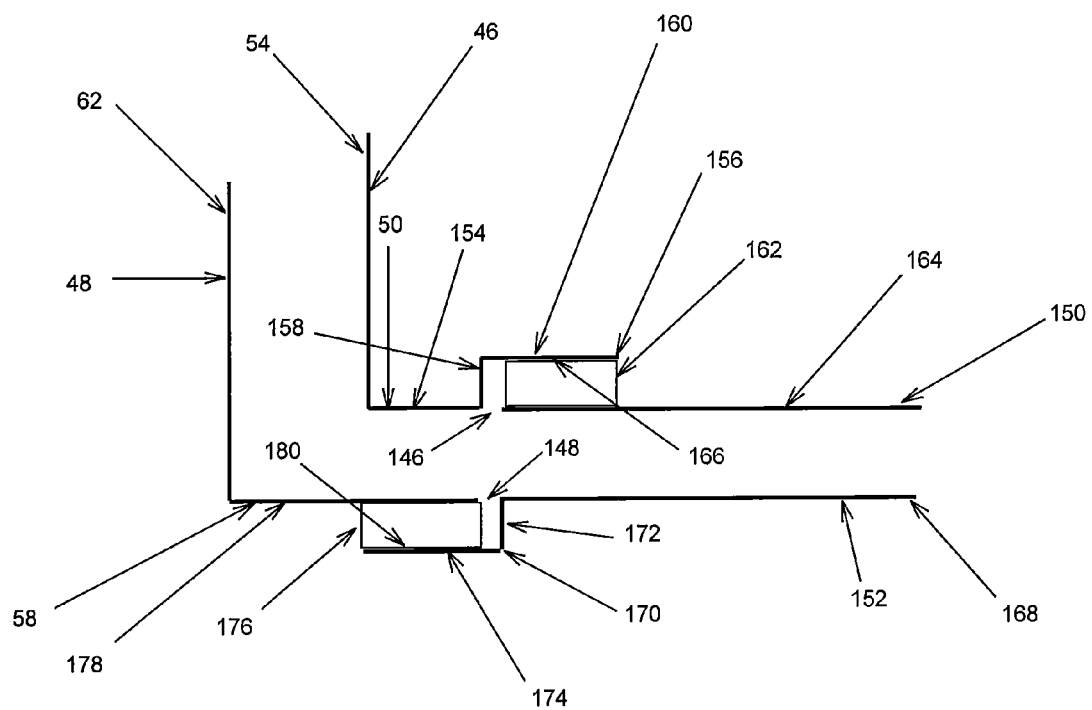
FIG. 8 is a schematic sectional view showing the attachment of the access panels to the housing of the conveyor system of the exemplary embodiment.

Referring to FIGS. 4, 5, 8, and 9, the bottom walls 50, 58 of the housing 44 have access openings 146, 148 (FIG. 8) that are covered removable overlapping inner and outer access panels 150, 152. In particular, the bottom wall 50 of the inner housing piece 46 has an access opening 146 that is covered by an inner access panel 150. The inner access panel 150 is made of a suitable metal material that has ferromagnetic properties. FIG. 8 shows an exemplary arrangement of removably attaching the access panels 150, 152. As depicted in FIG. 8, the inner access panel 150 is sized slightly less than the perimeter of the inner access opening 146 and is positioned in the inner access opening 146 so that it is flushed with the bottom wall 50 of the inner housing piece 46. The bottom wall 50 of the inner housing piece 46 includes a base 154 and an L-shaped peripheral end 156. The peripheral end 156 includes a first leg 158 that extends inwardly from the base 154 and a second leg 160 extending perpendicular from the first leg 158. The second leg 160 extends parallel to the inner access panel 150 and overlaps a portion of the inner access panel 150. A magnetic fastener 162 is provided between the inner access panel 150 and inner housing piece 46 at their overlapping region to removably attach the inner access panel 150 to the inner housing piece 46. Specifically, the magnetic fastener 162 magnetically engages the inner surface 164 of the inner access panel 150 and the outer surface 166 of the second leg 160 of the peripheral end 156 of the bottom wall 50 of the inner housing piece 46. Thus, the inner access panel 150 is secured to the bottom wall 50 of the inner housing piece 46 by the magnetic force of the magnetic fastener 162.

The bottom wall 58 of the outer housing piece 48 has an access opening 148 that is covered by an outer access panel 152. The outer access panel 152 and the bottom wall 58 are made of a suitable metal material that has ferromagnetic properties. The outer access panel 152 includes a base 168 and an L-shaped peripheral end 170. The peripheral end 170 includes a first leg 172 that extends outwardly from the base 168 and a second leg 174 that extends perpendicular to the first leg 172. The second leg 174 extends parallel to the bottom wall 58 of the outer housing piece 48 and overlaps a portion of the outer access panel 152. The outer access panel 152 is positioned in the access opening 148 so that its base 168 is flushed with the bottom wall 58 of the outer housing piece. A magnetic fastener 176 is provided between the outer access panel 152 and outer housing piece 48 at their overlapping region to removably attach the outer access panel 152 to the outer housing piece. Specifically, the magnetic fastener magnetically engages the outer surface 178 of the bottom wall 58 of the outer housing piece 48 and the inner surface 180 of the outer access panel 152 at the second leg 174. Thus, the outer access panel 152 is secured to the bottom wall 58 of the outer housing piece 48 by the magnetic force of the magnetic fastener 176.

Figure 4:
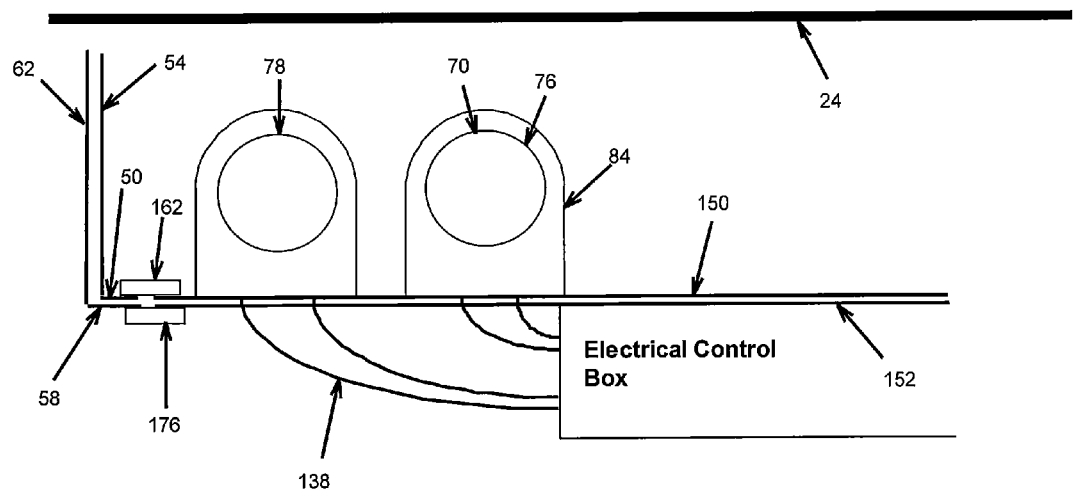
FIG. 4 is a schematic sectional view along line 4-4 of FIG. 2.
Figure 5:
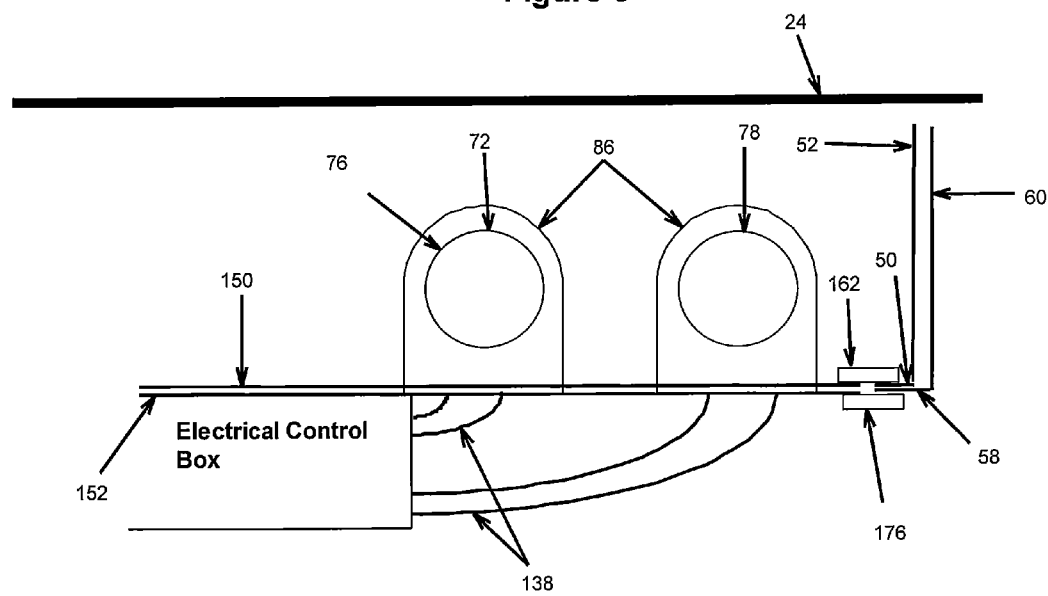
FIG. 5 is a schematic sectional view along line 5-5 of FIG. 2.
Figure 9:
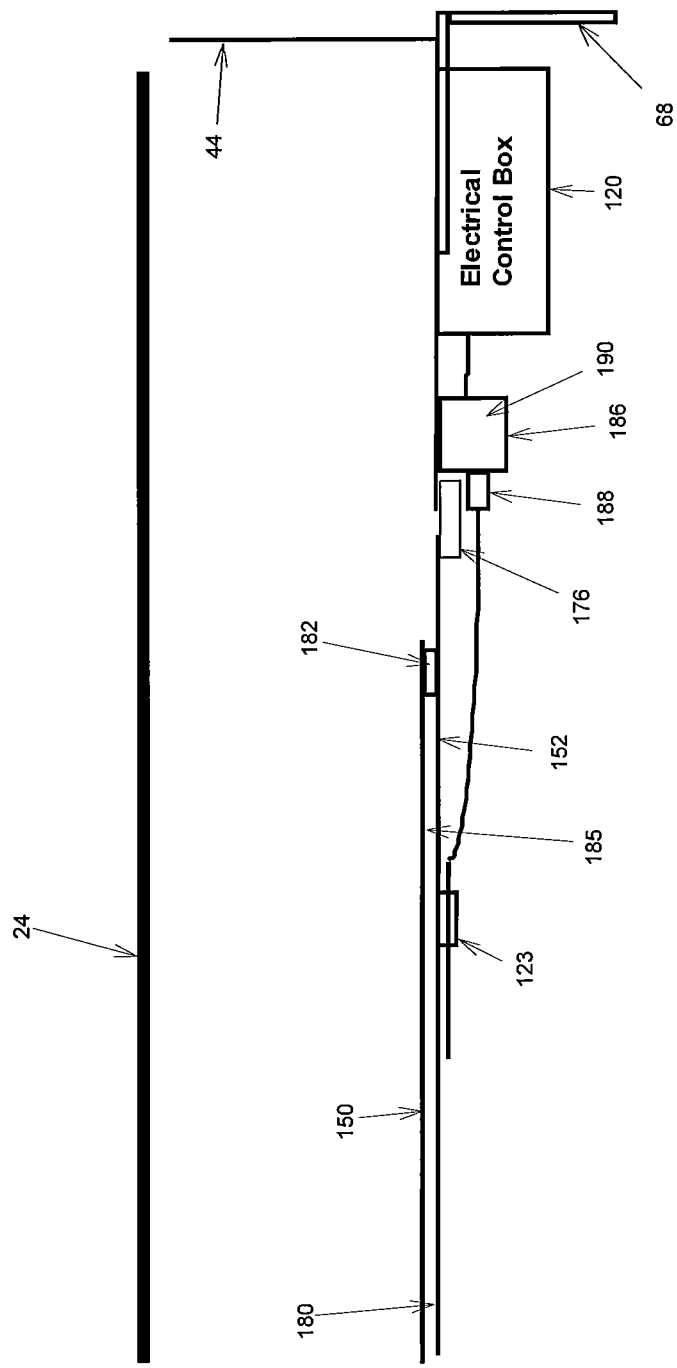
FIG. 9 is a schematic partial sectional view of the sterilizing system showing the access panels, power disconnect switch, and related elements.

FIGS. 4, 5, and 9 show an alternative exemplary arrangement of removably attaching the access panels to the housing by the magnetic fasteners. In this exemplary arrangement, each of access panels is flushed with and spaced horizontally from its associated bottom wall. The magnetic fastener 176 for the outer access panel magnetically engages the outer surface of the outer access panel and outer surface of the bottom wall of the outer housing piece. The magnetic fastener 162 for the inner access panel magnetically engages the inner surface of the inner access panel and inner surface of the bottom wall of the inner housing piece.

As shown in FIGS. 2 and 9, first and second magnetic seals 182, 184 may be provided between the overlapping panels to seal the housing 44 from the ultraviolet light and hold the access panels 150, 152 in place with respect to each other. Specifically, each magnetic seal is in the form a rectangular strip and magnetically engages the outer surface 185 (FIG. 9) of the inner access panel 150 and the inner surface 180 of the outer access panel 152. Alternatively, each of the magnetic seals 182, 184 may be attached to the outer surface 185 of the inner access panel 150 by an adhesive, or the magnetic seal could be riveted, bolted or crimped to the inner access panel 150. The first magnetic seal 182 may extend between the front and rear ends of the inner access panel 150 near the right end of the inner access panel 150. The second magnetic seal 184 may extend between the front and rear ends of the inner access panel 150 near the left end of the inner access panel 150. The magnetic seals 182, 184 and magnetic fasteners 162, 176 provide sufficient magnetic force to hold the access panels such that the panels do not slip or become dislodged during normal use of the conveyor belt. In addition, the magnetic seal is configured to form a continuous seal between the panels that prevents the ultraviolet light from escaping around the edges of the access panels. The magnetic attachment also holds the panels in place such that any vibration conveyed from the conveyor system does not result in vibration between the access panels and the housing. Additional magnetic seals may be positioned between the access panels to dampen vibration and shield the ultraviolet light. Alternatively, the magnetic seals 182, 184 may be replaced with other materials such as plastic or polyurethane foam or any other material capable of providing the ability to dampen vibration and block ultraviolet radiation from escaping from between the inner and outer housing pieces 46, 48.

To gain access to the light sources 70, 72 and other internal components of the sterilizing system 22, the outer access panel 152 is first removed by grasping or prying the outer access panel 152 and applying sufficient force outwardly to overcome the magnetic force exerted between the magnetic fastener 176 and the magnetic seals 182, 184. Then, the inner access panel 150 is removed by grasping or prying the inner access panel 150 and applying sufficient force outwardly to overcome the magnetic force exerted between the magnetic fastener 162. The removable access panels permit a technician to replace the light sources (or internal parts) without needing to detach the sterilizing system from the conveyor system. Further, no tools are needed to remove panels or otherwise gain access to light sources or other parts in the housing. Alternatively, the magnetic fasteners 162, 176 may be replaced with bolts, clamps, screws, hook and loop fasteners such as Velcro®, or other fastening devices provided they maintain a flush surface between the bottom wall of the inner housing piece 50 and the inner access panel 150 and between the bottom wall of the outer housing piece 58 and the outer access panel 152

The exemplary embodiment may utilize various systems to prevent human exposure to the ultraviolet when servicing or otherwise gaining access to the light sources or other internal components. One embodiment may comprise a power disconnect switch 186 that is provided such that the power being supplied to the ultraviolet light sources 70, 72 is disconnected prior to removal of the outer access panel. In particular, referring to FIG. 9, the power disconnect switch 186 includes a plug 188 and an electrical socket 190. The plug 188 is electrically connected to the electrical cord 123 coming from the power source 38. The socket 190 is electrically connected to the electrical control box 120. The electrical cord 123 may be attached to the outer access panel 152. When the outer panel 152 is attached to the housing 44, the plug 188 is plugged into the socket 190 to allow the power to be supplied to the ultraviolet light sources 70, 72 and other devices of the sterilizing system 22. When the outer access panel 152 needs to be removed to gain access to the light sources or other internal components, the user has to unplug the plug 188 from the electrical socket 190, thus disconnecting the power source 38 from the sterilizing system 22 before the outer access panel 152 can be pulled or pried outwardly to overcome the magnetic force exerted between the magnetic fastener 176 and the magnetic seals 182, 184.

Alternatively, or in addition to the power disconnect switch 186, an optical light sensor 127 (see FIG. 2) may be incorporated on the outer surface of the exemplary embodiment. The optical light sensor 127 may be electrically connected to the ballast 126 and control circuitry 122 in the control box 120. The optical light sensor 127 would be capable of detecting fluctuations in the visible light spectrum indicative of removal of an access panel on the conveyor stand 28. Upon detection of an increase of a predetermined amount of light indicative of removing an access panel of the conveyor stand 28, electrical circuitry connected to the optical light sensor 127 would cut power to one or more of the UV light ballasts.

Other types of power disconnect switches can be used. For example, the switch could include a spring loaded pushbutton. For this switch, when the outer access panel is attached, the outer access panel causes the pushbutton to depress and close the switch to electrically connect the power source to the sterilizing system. When the outer access panel is removed, the pushbutton extends to open the switch and electrically disconnect the power source from the sterilizing system.

Thus exemplary embodiments achieve at least some of the above stated objectives, eliminate difficulties encountered in the use of prior devices and systems, solve problems, and attain the desirable results described herein.

In the foregoing description, certain terms have been used for brevity, clarity, and understanding, however, no unnecessary limitations are to be implied therefrom because such terms are used for descriptive purposes and are intended to be broadly construed. Moreover, the descriptions and illustrations herein are by way of examples and the invention is not limited to the exact details shown and described.

In the following claims any feature described as a means for performing a function shall be construed as encompassing any means known to those skilled in the art as being capable of performing the recited function, and shall not be deemed limited to the particular means shown in the foregoing description or mere equivalents thereof. The provisions of an Abstract herewith shall not be construed as limiting the claims to features discussed in the Abstract.

Having described the features, discoveries and principles of the invention, the manner in which it is constructed and operated, and the advantages and useful results attained; the new and useful structures, devices, elements, arrangements, parts, combinations, systems, equipment, operations, methods, processes and relationships are set forth in the appended claims.

What is claimed is:

1. A sterilizing system configured for sterilizing a plurality of continuous loop conveyor belts having different widths, wherein each belt is movable between upper and lower flight paths, wherein the upper flight path includes an exposed surface for receiving items, the sterilizing system comprising:
    a housing, wherein the housing is configured to at least partially cover the lower flight path;
    an ultraviolet light unit positioned in an interior of the housing, wherein the ultraviolet light unit is operative to emit ultraviolet light on the surface of each of the belts at the lower flight path to sanitize the belt;
    wherein the ultraviolet light unit is adjustable between a first configuration and at least a second configuration, wherein the ultraviolet light unit is operative in the first configuration to emit light that extends across a belt of a first width from one end of the belt to the opposite end of the belt;
    wherein the ultraviolet light unit is operative in the second configuration to emit light that extends across another belt of a second width from one end of the another belt to the opposite end of the another belt, wherein the second width is different from the first width.

2. The sterilizing system of claim 1 wherein the ultraviolet light unit comprises first and second light sources that are spaced from one another along the lower flight path, wherein the second light source is movable relative to the first light source between at least a first position that places the ultraviolet light unit in the first configuration and at least a second position that places the ultraviolet light unit in the at least second configuration.

3. The sterilizing system of claim 2 including a bracket operatively mounted to the interior of the housing, wherein the bracket includes a track, wherein the track slidably receives the second light source, wherein the second light source is slidably movable along the track between at least the first and second positions.

4. The sterilizing system of claim 2 including a lock operatively connected to at least one of the first and second light sources, wherein the lock is operative in a locking position to prevent the second light source from moving relative to the first light source and in an unlocking position to allow the second light source to move relative to the first light source in an unlock position.

5. The sterilizing system of claim 2 wherein the housing includes an inner housing piece and an outer housing piece, wherein the outer housing piece is operative to slidably receive the inner housing piece, wherein the first light source is fixed to the inner housing piece and the second light source is fixed to the outer housing piece.

6. The sterilizing system of claim 1 including an ultraviolet reflective layer coated on an interior side of the housing.

7. A sterilizing system for sterilizing a continuous loop conveyor belt of a conveyor system, wherein the conveyor system includes a drive operatively connected to the conveyor belt, wherein the drive is operative to move the belt between upper and lower flight paths, wherein the upper flight path includes an exposed surface for receiving items, the system comprising:
    a housing, wherein the housing is configured to at least partially cover the lower flight path;
    an ultraviolet light source positioned in the interior of the housing, wherein the ultraviolet light source is operative to emit ultraviolet light on the belt at the lower flight path to sanitize the belt;
    a light shield operatively associated with the ultraviolet light, wherein the light shield is operative to be in a first position blocking a predetermined amount of ultraviolet light emitted by the ultraviolet light source from being on the belt, wherein the light shield is operative to be in a second position allowing the ultraviolet light emitted by the ultraviolet light source to be on the belt.

8. The sterilizing system of claim 7, wherein the light shield is in the second position when the belt is moving between the upper and lower flight paths, wherein the light shield is in the first position after the belt stops moving between the upper and lower flight paths.

9. The sterilizing system of claim 7, wherein the light shield comprises first and second shield portions on opposite sides of the ultraviolet light source, a first actuator arm operatively connected to the first shield portion and a second actuator arm operatively connected to the second shield portion, wherein movement of the first actuator arm causes movement of the first actuator arm toward and away from the first shield portion and movement of the second arm causes movement of the second shield portion toward and away from the first shield to place the light shield between the first and second positions.

* * * * *